(12) United States Patent
Duffield et al.

(10) Patent No.: US 8,703,708 B2
(45) Date of Patent: Apr. 22, 2014

(54) AGENTS AND METHODS FOR TISSUE REPAIR AND REGENERATION

(75) Inventors: Jeremy Duffield, Seattle, WA (US); Richard A. Lang, Indian Hill, OH (US)

(73) Assignees: The Brigham and Women's Hospital, Inc., Boston, MA (US); Cincinnati Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 13/256,760

(22) PCT Filed: Mar. 18, 2010

(86) PCT No.: PCT/US2010/027814
§ 371 (c)(1),
(2), (4) Date: Dec. 29, 2011

(87) PCT Pub. No.: WO2010/108001
PCT Pub. Date: Sep. 23, 2010

(65) Prior Publication Data
US 2012/0101042 A1 Apr. 26, 2012

Related U.S. Application Data

(60) Provisional application No. 61/161,190, filed on Mar. 18, 2009.

(51) Int. Cl.
*A61K 38/00* (2006.01)
*A61K 38/16* (2006.01)
*A61P 9/00* (2006.01)
*G01N 33/567* (2006.01)

(52) U.S. Cl.
USPC ....... 514/15.4; 514/16.4; 514/21.2; 514/21.3; 435/7.21

(58) Field of Classification Search
None
See application file for complete search history.

(56) References Cited

U.S. PATENT DOCUMENTS

| | | | |
|---|---|---|---|
| 6,488,822 B1 * | 12/2002 | Moslehi | 204/192.12 |
| 7,057,017 B2 * | 6/2006 | McCarthy | 530/350 |
| 7,138,505 B1 * | 11/2006 | Kuo et al. | 536/23.1 |
| 7,579,168 B2 * | 8/2009 | McCarthy | 435/69.1 |
| 2004/0087016 A1 * | 5/2004 | Keating et al. | 435/366 |
| 2005/0169995 A1 | 8/2005 | Kuo | |
| 2005/0196349 A1 | 9/2005 | Wu et al. | |
| 2005/0261181 A1 | 11/2005 | Wu et al. | |
| 2007/0128187 A1 * | 6/2007 | Allen et al. | 424/143.1 |
| 2009/0047276 A1 | 2/2009 | Moon et al. | |

FOREIGN PATENT DOCUMENTS

WO 2007/136226 11/2007

OTHER PUBLICATIONS

Ito et al., (Nature. May 17, 2007;447(142):316-20).*
Arnold et al., "Inflammatory monocytes recruited after skeletal muscle injury switch into antiinflammatory macrophages to support myogenesis," J. Exp. Med., 204(5): 1057-1069 (2007).
Boussif et al., "A versatile vector for gene and oligonucleotide transfer into cells in culture and in vivo: polyethylenimine," Proc. Natl. Acad. Sci. USA, 92:7297-7301 (2010).

(Continued)

*Primary Examiner* — Cherie M Stanfield
(74) *Attorney, Agent, or Firm* — Fish & Richardson P.C.

(57) ABSTRACT

Methods of treating solid organ injuries using compounds that enhance Wnt signalling are described.

16 Claims, 9 Drawing Sheets

(56) References Cited

OTHER PUBLICATIONS

Carroll et al., "Wnt9b plays a central role in the regulation of mesenchymal to epithelial transitions underlying organogenesis of the mammalian urogenital system," Dev. Cell, 9:283-292 (2005).

Castano et al., "Serum amyloid P inhibits fibrosis through Fc gamma R-dependent monocyte-macrophage regulation in vivo," Science Transl. Med., 1(5):5-13 (2009).

Chen et al., "Structural insight into the mechanisms of Wnt signaling antagonism by Dkk," J. Biol. Chem., 283:23364-23370 (2008).

Cude et al., "Regulation of the G2-M cell cycle progression by the ERK5-NFkappaB signaling pathway," J. Cell Biol., 177(2):253-264 (2007).

Deng et al., "A novel mouse model of inflammatory bowel disease links mammalian target of rapamycin-dependent hyperproliferation of colonic epithelium to inflammation-associated tumorigenesis," Am. J. Pathol., 176(2):952-967 (2010).

Dickinson and Sive, "The Wnt antagonists Frzb-1 and Crescent locally regulate basement membrane dissolution in the developing primary mouth," Development, 136(7):1071-1081 (2009).

Duffield et al., "Conditional ablation of macrophages halts progression of crescentic glomerulonephritis," Am. J. Pathol., 167(5):1207-1219 (2005).

Duffield et al., "Selective depletion of macrophages reveals distinct, opposing roles during liver injury and repair," J. Clin. Invest., 115(1):56-65 (2005).

Duffield et al., "Restoration of tubular epithelial cells during repair of the postischemic kidney occurs independently of bone marrow-derived stem cells," J. Clin. Invest., 115(7):1743-1755 (2005).

Duffield et al., "Activated macrophages direct apoptosis and suppress mitosis of mesangial cells," J. Immunol., 164:2110-2119 (2000).

Duffield et al., "Resolvin D series and protectin D1 mitigate acute kidney injury," J. Immunol., 177:5902-5911 (2006).

Fallowfield et al., "Scar-associated macrophages are a major source of hepatic matrix metalloproteinase-13 and facilitate the resolution of murine hepatic fibrosis," J. Immunol., 178(8):5288-5295 (2007).

Glass et al., "Canonical Wnt signalling in differentiated osteoblasts controls osteoclast differentiation," Dev. Cell, 8(5):751-764 (2005).

Goren et al., "A transgenic mouse model of inducible macrophage depletion: effects of diphtheria toxin-driven lysozyme M-specific cell lineage ablation on wound inflammatory, angiogenic, and contractive processes," Am. J. Pathol., 175(1):132-147 (2009).

Holmen et al., "Decreased BMD and limb deformities in mice carrying mutations in both Lrp5 and Lrp6," J. Bone Miner Res., 19(12):2033-2040 (2004).

Humphreys et al., "Intrinsic epithelial cells repair the kidney after injury," Cell Stem Cell, 2(3):284-291 (2008).

Ichimura et al., "Kidney injury molecule-1 is a phosphatidylserine receptor that confers a phagocytic phenotype on epithelial cells," J. Clin. Invest., 118(5):1657-1668 (2008).

Inoue et al., "Hepatocyte growth factor counteracts transforming growth factor-beta1, through attenuation of connective tissue growth factor induction, and prevents renal fibrogenesis in 5/6 nephrectomized mice," Faseb. J., 17(2):268-270 (2003).

International Search Report issued in PCT/US2010/027814 on Jan. 25, 2011.

Kato et al., "Cbfa1-independent decrease in osteoblast proliferation, osteopenia, and persistent embryonic eye vascularization in mice deficient in Lrp5, a Wnt coreceptor," J. Cell. Biol., 157(2):303-314 (2002).

Lakso et al., "Targeted oncogene activation by site-specific recombination in transgenic mice," Proc. Natl. Acad. Sci. USA, 89(14):6232-6236 (1992).

Lin et al., "Pericytes and perivascular fibroblasts are the primary source of collagen-producing cells in obstructive fibrosis of the kidney," Am. J. Pathol., 173:1617-1627 (2008).

Lin et al., "Bone marrow Ly6Chigh monocytes are selectively recruited to injured kidney and differentiate into functionally distinct populations," J. Immunol., 183(10):6733-6743 (2009).

Lobov et al., "WNT7b mediates macrophage-induced programmed cell death in patterning of the vasculature," Nature, 437(7057):417-421 (2005).

Mantovani et al., "Tumour-associated macrophages as a prototypic type II polarised phagocyte population: role in tumour progression," Eur. J. Cancer, 40(11):1660-1667 (2004).

Mao and Niehrs, "Kremen2 modulates Dickkopf2 activity during Wnt/LRP6 signaling," Gene, 302(1-2):179-183 (2003).

Mao et al., "Kremen proteins are Dickkopf receptors that regulate Wnt/beta-catenin signaling," Nature, 417(6889):664-667 (2002).

Maretto et al., "Mapping Wnt/beta-catenin signaling during mouse development and in colorectal tumors," Proc. Natl. Acad. Sci. USA, 100(6):3299-3304 (2003).

Mirza et al., "Selective and specific macrophage ablation is detrimental to wound healing in mice," Am. J. Pathol., 175(6):2454-2462 (2009).

Miyake et al., "Protective role of macrophages in noninflammatory lung injury caused by selective ablation of alveolar epithelial type II Cells," J. Immunol., 178(8):5001-5009 (2007).

Murtaugh, "The what, where, when and how of Wnt/β-catenin signaling in pancreas development," Organogenesis, 4:81-86 (2008).

Nahrendorf et al., "The healing myocardium sequentially mobilizes two monocyte subsets with divergent and complementary functions," J. Exp. Med., 204(12):3037-3047 (2007.

Pull et al., "Activated macrophages are an adaptive element of the colonic epithelial progenitor niche necessary for regenerative responses to injury," Proc. Natl. Acad. Sci. USA, 102(1):99-104 (2005).

Rajagopal et al., "Wnt7b stimulates embryonic lung growth by coordinately increasing the replication of epithelium and mesenchyme," Development, 135(9):1625-1634 (2008).

Reya et al., "A role for Wnt signalling in self-renewal of haematopoietic stem cells," Nature, 423(6938):409-414 (2003).

Tauber, Nat. Rev., "Metchnikoff and the phagocytosis theory," Mol. Cell. Biol., 4: 897-901 (2003).

Veerman et al., "A second canon. Functions and mechanisms of beta-catenin-independent Wnt signaling," Dev. Cell., 5:367-377 (2003).

Xu et al., "Vascular development in the retina and inner ear: control by Norrin and Frizzled-4, a high-affinity ligand-receptor pair," Cell, 116(6):883-895 (2004).

Yu et al., "The role of Axin2 in calvarial morphogenesis and craniosynostosis," Development, 132(8):1995-2005 (2005).

Yu et al., "A Wnt7b-dependent pathway regulates the orientation of epithelial cell division and establishes the cortico-medullary axis of the mammalian kidney," Development, 136(1):161-171 (2009).

Zeng et al., "A dual-kinase mechanism for Wnt co-receptor phosphorylation and activation," Nature, 438(7069):873-877 (in eng) (2005).

Extended European Search Report issued in EP10754107 on Jul. 25, 2013 (11pages).

Lin et al., "Macrophage Wnt7b is critical for kidney repair and regeneration," Proceedings of the National Academy of Sciences, 107(9):4194-4199 (2010).

Wu et al., "Mutual Antagonism Between Dickkopf1 and Dickkopf2 Regulates WNT/Beta-Catenin Signalling," current Biology, Current Science, 10(24):1611-1614 (2000).

* cited by examiner

FIG. 1A      FIG. 1B
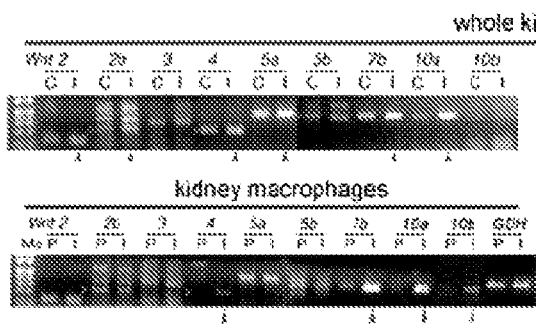
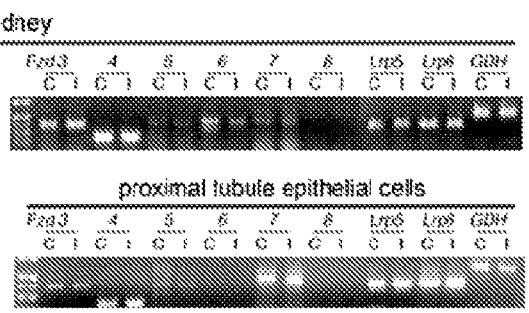
FIG. 1C      FIG. 1D
FIG. 1E
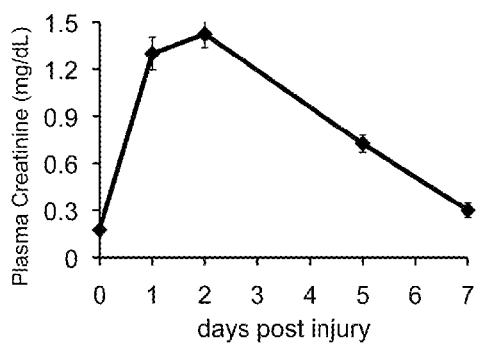
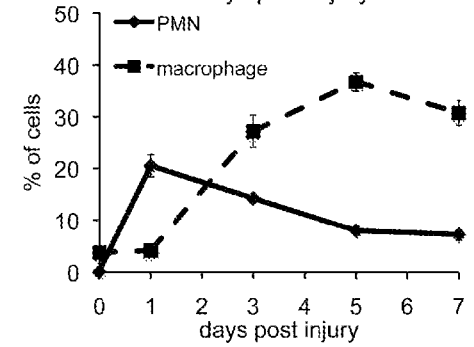
FIG. 1F
FIG. 1G
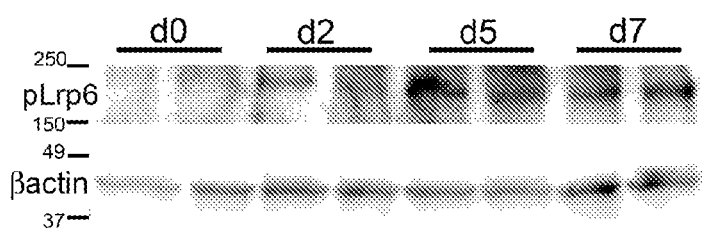

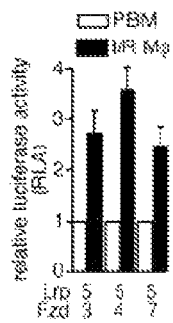
FIG. 2A
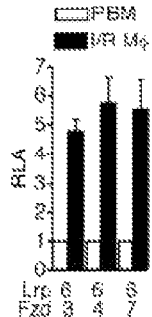
FIG. 2B
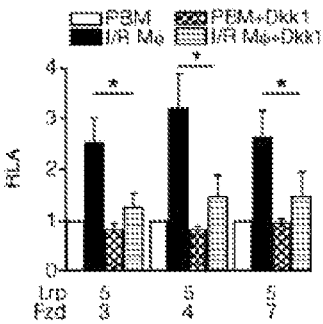
FIG. 2C
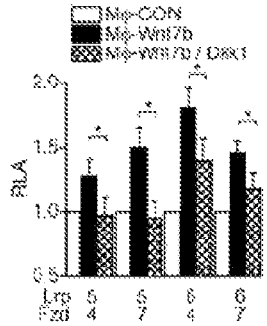
FIG. 2D
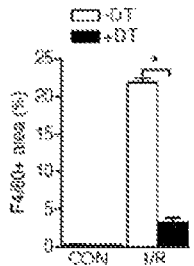
FIG. 2E
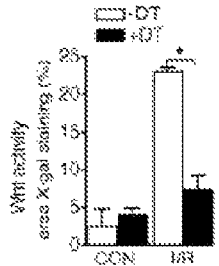
FIG. 2F
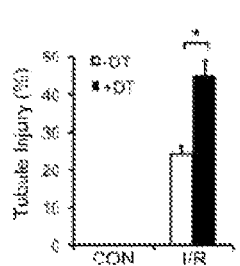
FIG. 2G
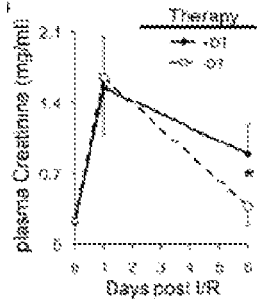
FIG. 2H
FIG. 2I
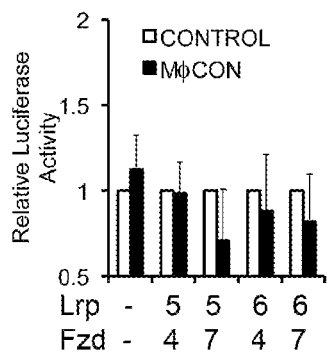
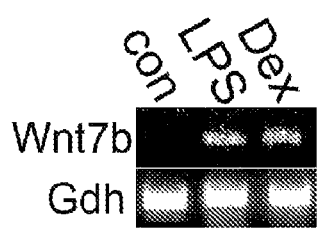
FIG. 2J

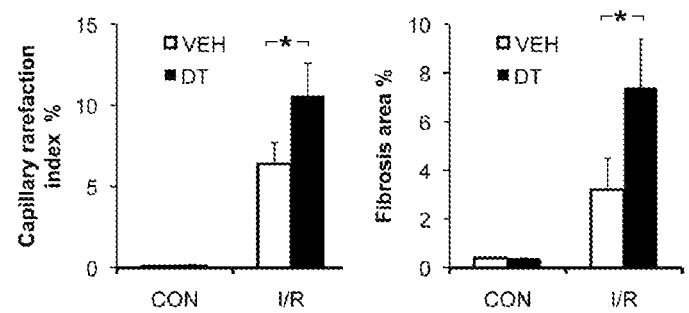
FIG. 2K
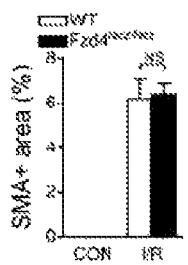 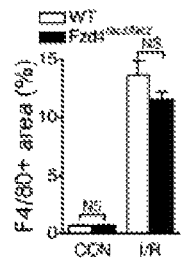 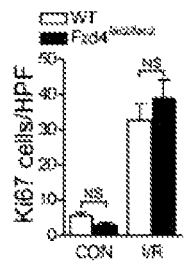  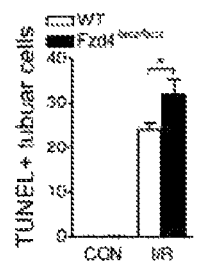
FIG. 3A    FIG. 3B    FIG. 3C    FIG. 3D    FIG. 3E FIG. 3F
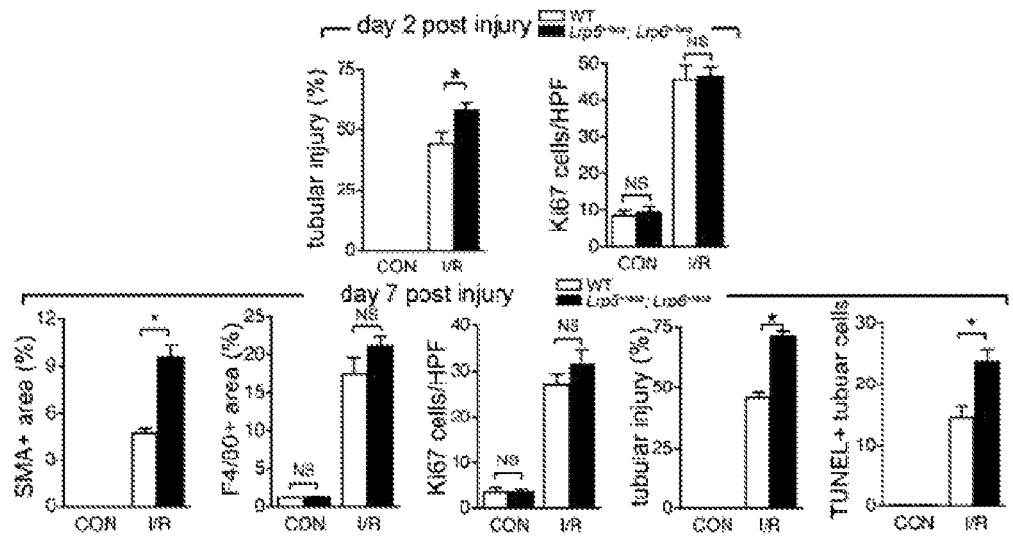
FIG. 3G
FIG. 4A
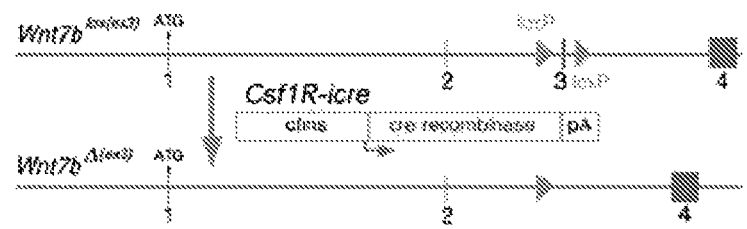
FIG. 4B
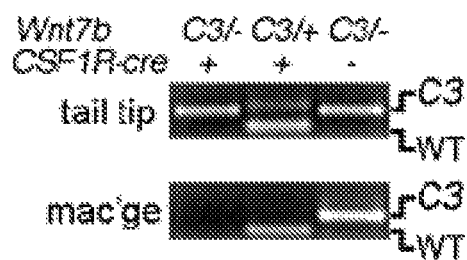

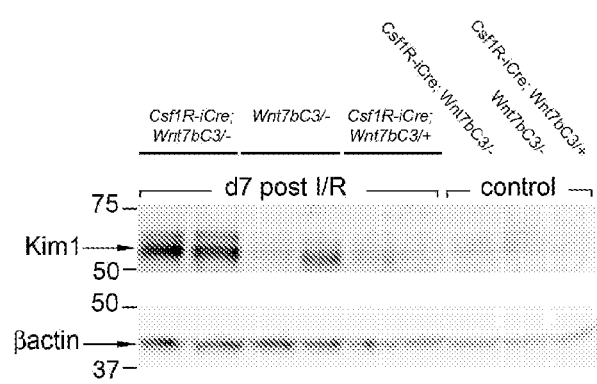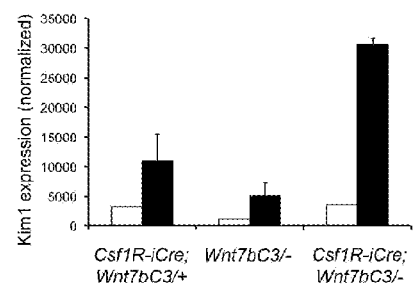
FIG. 4K
FIG. 4L
FIG. 5A
FIG. 5B
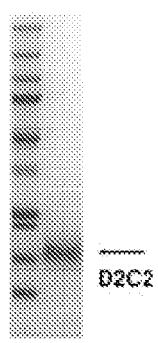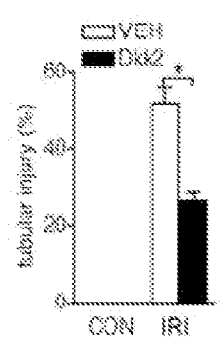

FIG. 5D  FIG. 5E  FIG. 5F

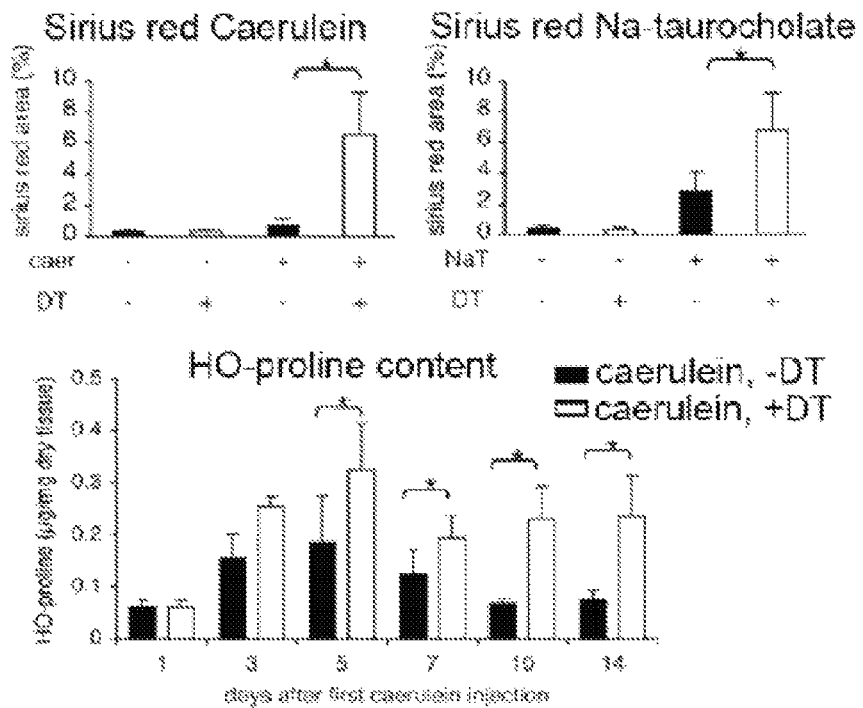
FIG. 6C
FIG. 6D
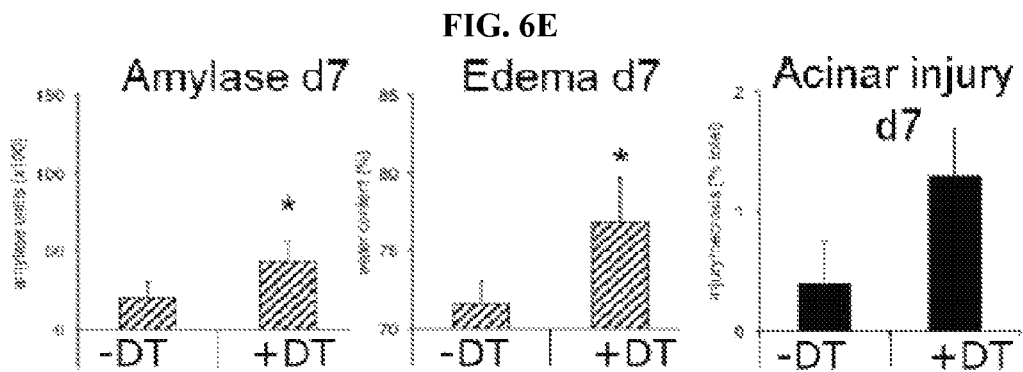
FIG. 6E

ID NO:91) or a human homolog thereof (SEQ ID NO:90). In some embodiments, the composition enhances regeneration of epithelial cells. In some embodiments, the composition enhances regeneration of vasculature in the organ.

AGENTS AND METHODS FOR TISSUE REPAIR AND REGENERATION

CLAIM OF PRIORITY

This application is a 371 application of International Application No. PCT/US2010/027814, filed on Mar. 18, 2010, and claims the benefit of U.S. Provisional Patent Application 61/161,190, filed on Mar. 18, 2009, the entire contents of which are incorporated by reference herein.

FEDERALLY SPONSORED RESEARCH OR DEVELOPMENT

This invention was made with Government support under Grant Nos. DK73299, DK84077, DK87389, EY16241, EY15766, EY17848, CA131270, and DK054364 awarded by the National Institutes of Health. The Government has certain rights in the invention.

TECHNICAL FIELD

This invention relates to agents and methods for tissue repair and regeneration, and more particularly to agents that activate canonical Wnt signalling, e.g., by inducing or enhancing Lipoprotein receptor like proteins 5 and 6 (LRP5 and LRP6) or Frizzled (Fzd) 4, 7, or 8 activity, or downstream cell signaling pathways.

BACKGROUND

Macrophages play a critical role in resolution of inflammation and/or tissue injury repair (see, e.g., Mantovani et al., Eur J Cancer 40(11):1660-1667 (2004); Duffield et al., J Clin Invest 115(1):56-65 (2005); Nahrendorf M, et al., J Exp Med 204(12):3037-3047 (2007); Arnold et al., J Exp Med 204(5): 1057-1069 (2007); Fallowfield et al., J Immunol 178(8): 5288-5295 (2007); and Castano et al., Science Transl Med 1(5):5ra13 (2009)) and macrophage Wnt ligands establish tissue homeostasis during development (Lobov I B, et al., Nature 437(7057):417-421 (2005)).

SUMMARY

The present invention is based, at least in part, on the discovery that (1) kidney injury results in an up-regulation of Wnt ligands in macrophages and the canonical Wnt response in epithelial cells; (2) ex vivo, macrophages from the injured kidney are a source of increased Wnt activity; (3) macrophage ablation during repair of the injured kidney results in reduced canonical Wnt response in kidney epithelial cells; (4) compromise of Wnt receptors or conditional deletion of Wnt7b in the macrophage lineage results in a reduction of the repair response and persistent injury; and (5) macrophage Wnt7b is required for repair of the kidney tubule basal lamina and relief of a G2 arrest in kidney epithelial cells. Combined, these results indicate that repair of damage to kidney tubules is mediated by an influx of macrophages that produce Wnt7b and signal locally to remaining kidney epithelial progenitors.

Thus, in one aspect, the invention provides methods for enhancing solid organ tissue repair and regeneration following injury, by administering a composition that enhances canonical Wnt signalling. In another aspect, the invention provides a composition that enhances canonical Wnt signalling for enhancing solid organ tissue repair and regeneration following injury.

In some embodiments, the solid organ is a kidney, liver, intestine (large or small), skeletal muscle, heart, pancreas, or lung. In some embodiments, the injury is an injury in which activated macrophages play a role in recovery. In some embodiments, the injury is selected from the group consisting of an ischemic injury, a toxic injury, an infectious injury, an autoimmune injury, and an inflammatory injury.

In some embodiments, the composition that enhances Wnt signalling comprises Dikkopf 2 (Dkk2) or an active fragment thereof comprising the C-terminal cysteine-rich domain that binds to and activates LRPSI6. In some embodiments, the active fragment of Dkk2 comprises amino acids Met172-Ile259 of mouse Dkk2 (SEQ ID NO:91) or a human homolog thereof (SEQ ID NO:90). In some embodiments, the composition enhances regeneration of epithelial cells. In some embodiments, the composition enhances regeneration of vasculature in the organ.

In some embodiments, the composition is administered systemically or into the organ, e.g., by local application or injection, or infusion through the vasculature. In some embodiments, the composition enhances LRP5/6 or Fzd 4/7/8 activity in epithelial cells.

In another aspect, the invention provides methods for identifying a therapeutic composition for enhancing solid organ tissue repair and regeneration following injury; the methods include identifying an agent that enhances canonical Wnt signalling, e.g., in epithelial cells.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-D are images of blots showing the results of semi quantitative RT-PCR for transcript levels of Wnt signalling pathway ligands and receptors in whole kidney or purified cell types (normal control [C] or d5 post injury [I] or peripheral blood monocytes [P]) Red arrows indicate upregulated transcripts. All studies were repeated at least three times and gave comparable results. Marker=50 μm*P<0.05.

FIGS. 1E-F are bar graphs showing characterization of ischemia reperfusion injury following by repair. 1E, Plasma Creatinine levels (inversely related to kidney function) in C57BL6 mice in days following kidney ischemia reperfusion injury. 1F, Graph showing the proportion of neutrophils Ly6G+ and macrophages (CD11b+, NK1.1−, Ly6G−) in single cell preparation of whole kidney during a time course following ischemia reperfusion injury assessed by flow cytometry.

FIG. 1G is an image of a Western blot of kidney cortex showing phospho-Lrp6, indicative of active canonical Wnt signaling. Note that in control adult cortex pLrp6 is not detected but it is detected from d2 after I/R onward.

FIGS. 2A-D are bar graphs showing relative luciferase activity (RLA) from STF cells expressing Lrp5 or Lrp6 with Fzd3, Fzd4 or Fzd7, induced by co-culture with: (2A-C) d5 post FR kidney macrophages (I/R Mφ) compared with autologous peripheral blood monocytes (PBM) and inhibited (2C) by recombinant Dkk1; or (2D) co-culture with bone marrow macrophages (Mφ-CON) or Wnt7b expressing bone marrow macrophages and inhibited by the addition of Dkk1-expressing 293T cells.

FIGS. 2E-G are line graphs showing quantification of macrophages, active Wnt signaling (Xgal staining) in kidney cortex and medulla, and tubule injury d6 after injury. (N) Kidney function testing (plasma creatinine levels) in cohorts of mice (n=6/group) with or without macrophage ablation from d3-d6. Normal recovery is prevented by ablation. P<0.05. n=5 or 6/group. Marker=50 µm.

FIG. 2H is a bar graph showing the results of kidney function testing (plasma creatinine levels) in cohorts of mice (n=6/group) with or without macrophage ablation from d3 to d6. Normal recovery is prevented by ablation. P<0.05. n=5 or 6/group. (Scale bars, 50 µm)

FIG. 2I is a bar graph showing relative luciferase activity from co-culture of unactivated BM macrophages with STF reporter cells expressing combinations of Lrp and Fzd do not induce canonical Wnt signaling.

FIG. 2J is an image of a gel showing the results of RT-PCR amplification of Wnt7b and Gapdh (32 cycles) in cultured BM derived macrophages on glass treated with LPS or Dexamethasone.

FIG. 2K is a pair of bar graphs showing the results of characterization of impaired kidney repair following macrophage ablation in CD11b-DTR mice. The graphs show capillary rarefaction (left graph) and interstitial fibrosis (right graph) in CD11b-DTR mice on d6 post I/R that received either vehicle of DT from d3-d6 following I/R (*P<0.05 n=5/group)

FIGS. 3A-3E are bar graphs showing quantification of inflammation, injury and repair parameters 5d post kidney IRI injury in Fzd4$^{LacZ/LacZ}$ or littermate control mice.

FIGS. 3F-G are a pair (3F) and set of 5 (3G) bar graphs showing quantification of inflammation, injury and repair parameters in WT or Lrp5$^{+/lacz}$; Lrp6$^{+/lacz}$ kidneys. P<0.05. n=5 or 6/group.

FIG. 4A is a genomic map and FIG. 4B shows PCR products (tail or macrophage genomic DNA) showing the third exon of Wnt7b is deleted in monocytes/macrophages of mice with the LoxP-flanked conditional allele Wnt7bC3 and the transgene Csf1r-iCre. WT allele 153 bp, C3 allele 200 bp, ΔC3 allele no product).

FIGS. 4C-4G are bar graphs showing quantification of inflammation, injury and repair parameters 7d post injury of Csf1R-iCre; Wnt7b$^{C3/-}$ or control mice (Csf1R-iCre; Wnt7b$^{C3/+}$ and Wnt7b$^{C3/-}$).

Figure 4C:
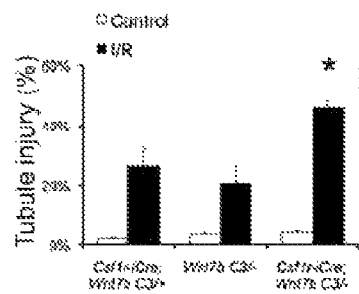
Figure 4D:
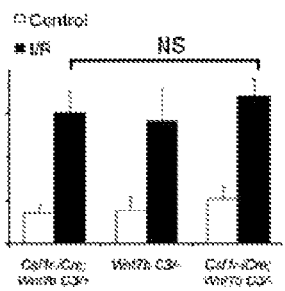
Figure 4E:
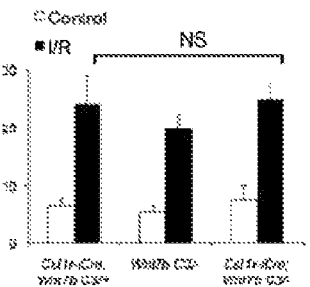
Figure 4F:
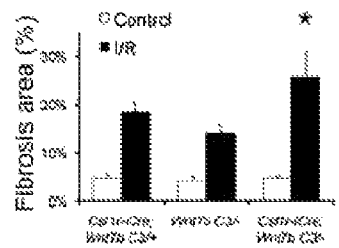
Figure 4G:
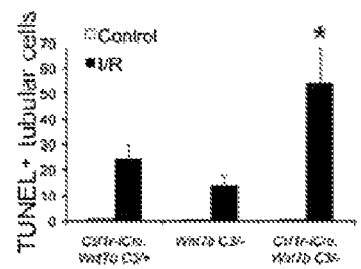
Figure 4H:
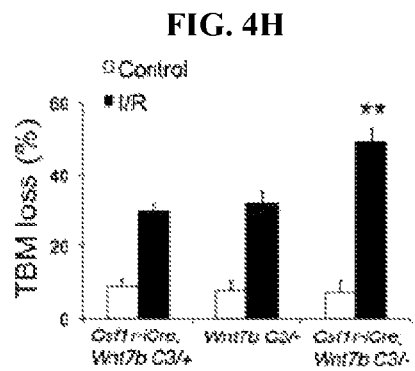

FIG. 4H is a bar graph showing quantification of dissolution of epithelial basement membrane in control and experimental (Csf1R-iCre; Wnt7b$^{C3/-}$) mice.

Figures 4I, 4J:
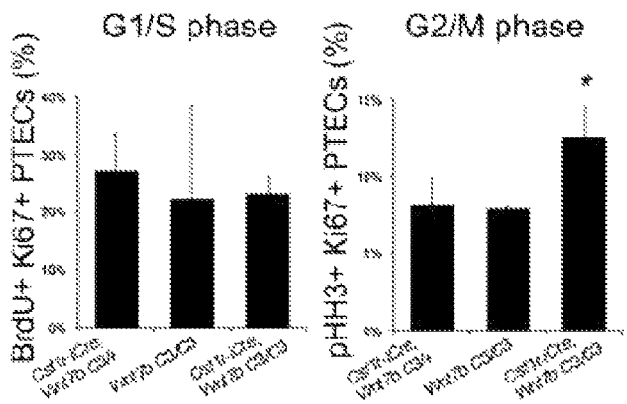

FIGS. 4I-J are bar graphs showing quantification of epithelial cells entering G1/S (4I) or in G2M (4J) phase of the cell cycle P<0.05. n=5 or 6/group.

FIG. 4K is a representative Western blot of the proximal tubule epithelial injury/dedifferentiation protein, Kim1 in kidneys from Csf1R-iCre; Wnt7bC3/– mice lacking Wnt7b in macrophages (left lanes) and controls.

FIG. 4L is a bar graph showing Kim1 protein expression determined by Western Blot from (n=4/group), normalized for beta-actin expression.

FIG. 5A is a Coomassie-stained polyacrylamide gel showing purified Dkk2-C2 (D2C2).

Figure 5C:
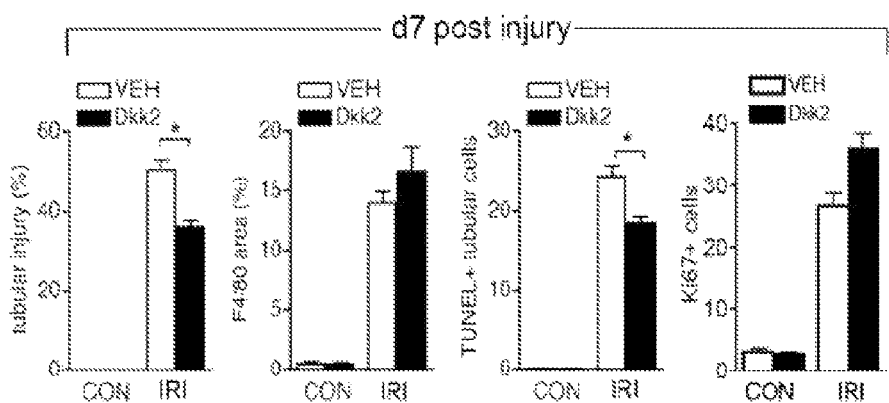
Figure 5C:
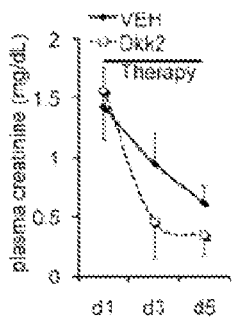
Figure 5C:
Figure 5C:
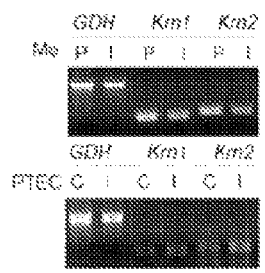

FIGS. 5B-C are one (5B) and a trio (5C) of graphs showing quantified injury and repair parameters in kidneys treated with VEHicle or Dkk2.

FIG. 5D is a line graph showing plasma creatinine levels in mice treated with Dkk2 from d1 post I/R onwards.

FIG. 5E is an image of a Western blot (upper) for pLrp6 (210 kDa) and loading control (beta-actin 45 KDa) in kidney cortex from mice on d5 post I/R treated with Dkk2-C2 or vehicle, and FIG. 5F is an image of a gel showing the results of RT-PCRs (middle and lower panels) for Kremen-1 and Kremen-2 in purified d5 post I/R kidney macrophages (Mφ) [I] compared with autologous peripheral blood monocytes [P] (upper) and d5 post IRI proximal tubule epithelial cells (PTEC) [I] or epithelial cells from control kidneys [C] (right panels). *P<0.05. n=6/group.

Figure 5G:
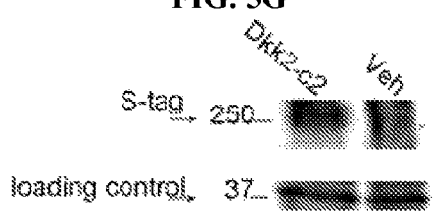

FIG. 5G is a representative Western blot for S-tag proteins in whole d5 post FR kidney from mice treated with Dkk2-C2 or vehicle. Note broad band detected at >200 kDa representing Dkk2-C2 bound to Lrp5 or Lrp6.

Figure 6A:
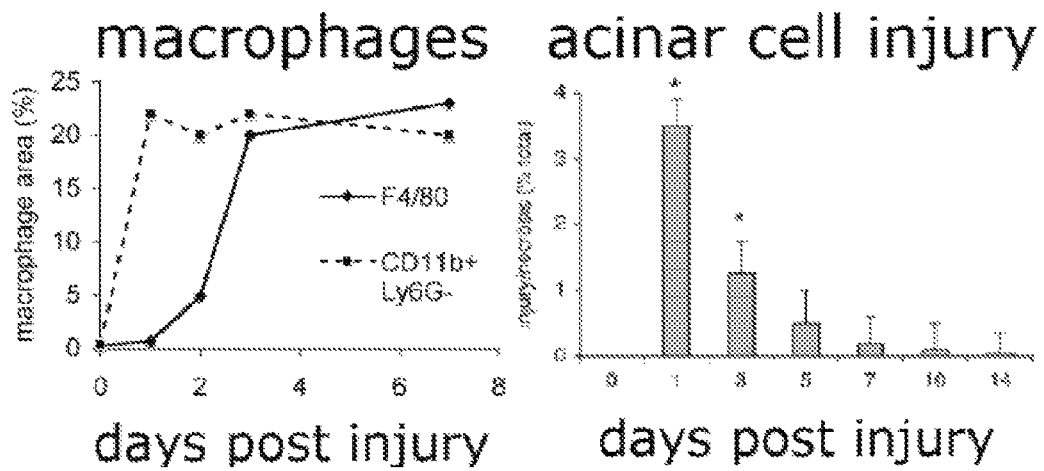

FIG. 6A is a line graph and a bar graph illustrating a time course of macrophages (F4/80 or CD11b+, Ly6G– immunostain) and acinar cell injury (score) in the pancreas indicating substantial macrophage recruitment during both injury and repair phases.

Figure 6B:
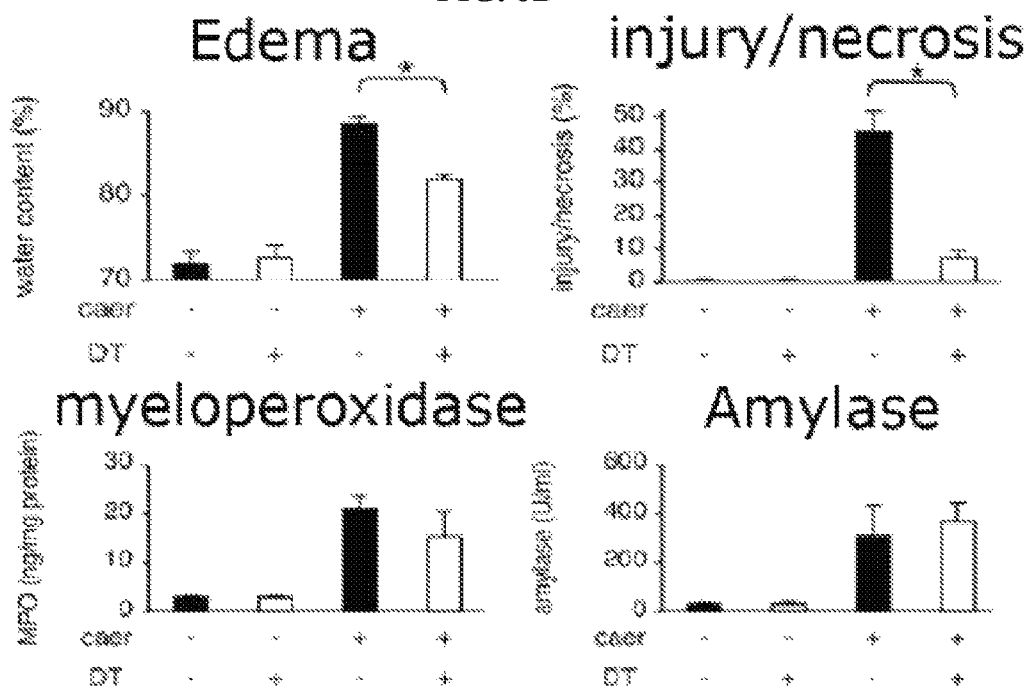

FIG. 6B is a set of four bar graphs showing that macrophage and monocyte ablation prior to induction of Caerulein pancreatitis and analysis at 24 h after injury indicates that macrophages promote necrotic injury during the induction phase (24 h after induction) as assessed (c) by pancreatic edema, injury/necrosis score MPO activity, and plasma amylase level.

FIGS. 6C-E are bar graphs showing that macrophage ablation with a single dose of DT 24 h after the induction of injury and analysis on d7 after induction in the Caerulein (C-D) and Na-taurocholate (C) models indicates that macrophages promote repair as assessed by fibrosis (Sirius red stain (C), or tissue HO-proline (D)), edema, plasma amylase and epithelial injury score.

DETAILED DESCRIPTION

The studies described herein show a functional role for canonical Wnt pathway signalling in any process of solid organ repair following injury. Macrophages are known as critical mediators of the inflammatory process that leads to repair and can produce a number of factors implicated in repair including bFGF, IGF, HGF and IL-10 (Inoue et al., Faseb J 17(2):268-270 (2003)).

Wnt7b is known to have an important role in the formation of kidney tubules. Its main function is to stimulate the polarized cell division that leads to elongation of the tubules as they form (Yu et al., Development 136(1):161-171 (2009)). In a number of systems, the Wnt pathway has a function in promoting the renewal of stem or progenitor cells (Reya et al., Nature 423(6938):409-414 (2003)) and this is consistent with the process of repair where we have shown it is likely that a relatively small population of progenitors expands to provide replacement tubule epithelial cells (Humphreys et al., Cell Stem Cell 2(3):284-291 (2008)). The present finding of an important role for macrophages in the resolution of injury is not inconsistent with the Metchnikovian view in which macrophages were assigned the function of the 'organismal policemen' with the role of restoring order from chaos (Tauber Nat Rev Mol Cell Biol 4(11):897-901 (2003)). Further, the universal involvement of macrophages in repair suggests that Wnt ligands may play roles in repair in other organs.

The present findings also support the therapeutic use of Wnt agonists to enhance repair in tissues, like the kidney, that involve the Wnt pathway. As described here, injection of the Wnt pathway agonist Dkk2-C2 resulted in enhanced repair. The lack of any apparent systemic effects of this treatment are probably explained by the restriction of Wnt pathway responses to a limited number of normal tissues in the adult. This model therapy therefore is useful in the treatment of human disease.

Methods of Treatment

The methods described herein include methods for the treatment of injuries to solid organs, e.g., kidney (e.g., chronic kidney disease), liver (e.g., chronic liver disease or cirrhosis), intestine (large or small, e.g., inflammatory bowel disease), skeletal muscle, heart, pancreas (e.g., pancreatitis), or lung (e.g., COPD). In some embodiments the injury is associated with fibrosis. The injuries that can be treated using the present methods are those in which activated macrophages play a role in recovery. Such injuries include injuries in which cell or tissue regeneration is desirable, e.g., an ischemic injury, a toxic injury, an infectious injury, an autoimmune injury, and an inflammatory injury. In some embodiments, the injuries are those in which activated macrophages play a role in recovery. See, e.g., Nahrendorf M, et al., J Exp Med 204(12):3037-3047 (2007)(heart); Arnold et al., J Exp Med 204(5):1057-1069 (2007)(skeletal muscle); Murtaugh, Organogenesis. 4, 81-86 (2008)(pancreas)); Duffield et al., J Clin Invest 115(1): 56-65 (2005)(liver); Fallowfield et al., J Immunol 178(8): 5288-5295 (2007)(liver); Pull et al., Proc Natl Acad Sci USA. 102(1):99-104 (2005) (intestine); Mirza et al., Am J. Pathol. 175(6):2454-62 (2009) (skin); Goren et al., Am J. Pathol. 175(1):132-47 (2009); and Miyake et al., J. Immunol. 178(8): 5001-9 (2007) (lung).

Generally, the methods include administering a therapeutically effective amount of an active agent that enhances canonical Wnt signalling compound as described herein, e.g., a compound that activates or enhances activation of LRP 5/6 or Fzd 4/7/8, to a subject who is in need of, or who has been determined to be in need of, such treatment.

As used in this context, to "treat" means to ameliorate at least one symptom of the injury. Often, the injury results in cell or tissue loss; thus, a treatment can result in an increase in tissue regeneration.

Compounds that Enhance Wnt Signalling

Compounds useful in the present methods include those that enhance canonical Wnt signalling compound as described herein, e.g., compounds that activate or enhance activation of LRP 5/6 or Fzd 4/7/8.

WNTs are secreted cysteine-rich glycoproteins that act as short-range ligands to locally activate receptor-mediated signaling pathways. In mammals, 19 members of the WNT protein family have been identified. WNTs activate more than one signaling pathway (Veerman et al., Dev. Cell., 5:367-377, 2003). The list of proteins identified as being involved in the WNT pathway is extensive and expanding.

Wnt signaling is transduced intracellularly by the frizzled (Fzd) family of receptors (Hendrickx and Leyns, Dev. Growth Differ., 50:229-243, 2008) and Lipoprotein receptor like proteins 5 and 6 (LRP5 and LRP6). Exemplary Wnt pathway agonists include, but are not limited to, e.g., Wnt ligands, e.g., Wnt7b; Dishevelled proteins, e.g., R-spondin (see, e.g., Kim et al., Cell Cycle 5(1):23-6 (2006); DSH/DVL1, 2, or 3; LRP5 and 6; and compounds that stimulate phosphorylation of LRP5 and/or 6 (see, e.g., WO2009155055), or stimulate degradation of the β catenine complex. Additional Wnt pathway activators are known in the art (see, e.g., Moon et al., Nature Reviews Genetics, 5:689-699, 2004). In some embodiments, suitable Wnt pathway agonists can include agonistic antibodies and antigen binding fragments thereof, and agonist peptides that bind specifically to LRP 5/6 or frizzled (Fzd) family of receptors, e.g., Fzd 4/7/8. In some embodiments, the agonist is Dikkopf 2 (DKK2), or an active fragment thereof comprising the C-terminal cysteine-rich domain that binds to and activates LRP5/6, e.g., DKK2C2, as described in WO 2009155055, incorporated herein by reference in its entirety. Inhibitors of Dkk1, Dkk3 or the soluble Frizzled like receptors (sFrps) may also enhance Wnt pathway signaling.

Certain kinase inhibitors can also be used, e.g., casein kinase 1 (CK1) and glycogen synthase kinase 3 β (GSK3β) inhibitors. In some embodiments, useful kinase inhibitors can increase β-catenin levels by reducing the degradation of β-catenin. In some embodiments, exemplary useful kinase inhibitors, e.g., GSK3β inhibitors include, but are not limited to, lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2'Z, 3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl) urea (AR-A014418), and indirubins (e.g., indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5-bromoindirubin), 4-Benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), and H-KEAPPAPPQSpP-NH2 (L803) (SEQ ID NO:1) or its cell-permeable derivative Myr-N-GKEAPPAPPQSpP-NH2 (L803-mts) (SEQ ID NO:2). Other GSK3β inhibitors are disclosed in Pat. Nos. 6,417,185; 6,489,344; 6,608,063 and Published U.S. Applications Nos. 690497, filed Oct. 20, 2003; 468605, filed Aug. 19, 2003; 646625, filed Aug. 21, 2003; 360535, filed Feb. 6, 2003; 447031, filed May 28, 2003; and 309535 filed Dec. 3, 2002. In some embodiments, suitable kinase inhibitors can include RNAi and siRNA designed to decrease GSK3β and/or CK1 protein levels. In some embodiments, useful kinase inhibitors include FGF pathway inhibitors. In some embodiments, FGF pathway inhibitors include, for example, SU5402.

Pharmaceutical Compositions and Methods of Administration

The methods described herein include the manufacture and use of pharmaceutical compositions, which include compounds as described herein that enhance Wnt signalling, or compounds identified by a method described herein, as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., antibiotics or steroids.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of Screening (Test Compounds)

Included herein are methods for screening test compounds, e.g., polypeptides, polynucleotides, inorganic or organic large or small molecule test compounds, to identify agents useful in the treatment of solid organ injuries. As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., a solid organ, and one or more effects of the test compound is evaluated. In a cultured or primary cell (e.g., an epithelial cell) for example, the ability of the test compound to activate or enhance Wnt signalling can be evaluated. In a solid organ, the ability of the compound to enhance or effect tissue repair and regeneration can be evaluated.

In some embodiments, the test sample is, or is derived from (e.g., a sample taken from) an in vivo model of a disorder as described herein. For example, an animal model, e.g., a rodent such as a rat, can be used.

Methods for evaluating each of these effects are known in the art. For example, ability to modulate Wnt signaling can be evaluated, e.g., using a reporter system, e.g., as described herein.

A test compound that has been screened by a method described herein and determined to activate or enhance Wnt signalling can be considered a candidate compound. A candidate compound that has been screened, e.g., in an in vivo model of a disorder, e.g., a model of solid organ injury, and determined to have a desirable effect on the disorder, e.g., on one tissue repair ad regeneration, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that activate or enhance Wnt signalling, and/or effect or enhance tissue repair ad regeneration) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating solid organ injuries, as described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of solid organ injuries, e.g., as described herein. The animal can be monitored for a change in the disorder, e.g., for an improvement in a parameter of the disorder, e.g., a parameter related to clinical outcome.

EXAMPLES

The invention is further described in the following examples, which do not limit the scope of the invention described in the claims.

Example 1

Wnt Pathway Responses are Induced in the Kidney Following Injury

The effects of alterations in Wnt signalling on kidney injury and repair were evaluated.

Ischemia-reperfusion injury of the kidney was performed as previously described (Duffield et al., J Clin Invest 115(7): 1743-1755 (2005)). In brief, anesthetized male mice (8-12 wks) had both kidneys exposed through surgical flank incisions. A surgical clamp placed across the renal arteries and veins. Kidneys were confirmed to become dusky, replaced in the retroperitoneum for 23 mins (bilateral) 28 mins (unilateral) injury. Clamps were removed and return of perfusion to kidneys confirmed, prior to wound closure. To deplete macrophages Cd11b-DTR mice received IV injection of DT (List Biologicals) (10 ng/g) or vehicle (100 µl) on d3 and d5 and kidneys harvested on d6, or injection on d2 and d4 and kidneys harvested in d5. Dkk-2 or vehicle (HBSS 1% BSA) was administered to C57BL6 male mice by IP injection (0.21 µg/g in 100 µl twice daily) from d0 until d2 or d7, and in a second series of experiments Dkk-2 or vehicle was administered from d1 until d5 by IV injection (0.42 µg/g in 100 µl twice daily). In these experiments mice received bilateral IRI clamping for 27 mins. All surgeries were performed in accordance with Protocols approved by the Harvard Center for Animal Research and Comparative Medicine.

Kidney injury can be assessed quantitatively using an injury score that depends on multiple criteria including the deposition of necrotic material within the kidney tubules and the appearance of epithelial cells of flattened morphology that is distinct from the cuboidal morphology of epithelial cells in the uninjured kidney. The kidney can be assessed functionally by measuring plasma creatinine, with high levels indicating compromise (Duffield et al., J Clin Invest 115(7):1743-1755 (2005); Humphreys et al., Cell Stem Cell 2(3):284-291 (2008)). According to injury scores (Duffield et al., J Clin Invest 115(7):1743-1755 (2005)) and creatinine assays (FIG. 1E), both of which are generally improving by 48 hours, the phase of kidney repair begins on day 2. Repair is associated with increased levels of epithelial proliferation, regeneration of epithelial tubules, mild expansion of interstitial myofibroblasts and transient deposition of interstitial collagens (Duffield et al., J Clin Invest 115(7):1743-1755 (2005); Humphreys et al., Cell Stem Cell 2(3):284-291 (2008)). Repair is also temporally associated with recruitment of large numbers of macrophages (FIG. 1F).

Kidney injury was induced in BATgal mice (Jackson Labs, (Maretto et al., Proc Natl Acad Sci U S A 100(6):3299-3304 (2003)) and Axin2-lacz Wnt pathway reporter mice (from the Max-Delbruch Center for Molecular Medicine, Berlin (Yu et al., Development 132(8):1995-2005 (2005)). Genotyping of the BATgal mice was performed as described (Maretto et al., Proc Natl Acad Sci U S A 100(6):3299-3304 (2003)), and genotyping of the Axin2-lacz mice was performed with the following primer pairs Ex2As3 (1) 5'-AGTCCATCTTCATTCCGCCTAGC-3' (SEQ ID NO:3), NLSBJ1 (2) 5'-TGGTAATGCTGCAGTGGCTTG-3' (SEQ ID NO:4), CKOIN4 (3) 5'-AAGCTGCGTCGGATACTTGAGA-3' (SEQ ID NO:5). 1+3 WT allele, 2+3 mutant allele.

Tissue preparation, immunostaining, imaging and disease quantification were performed as follows. Mouse kidneys were prepared for histology as previously described (Duffield et al., J Clin Invest 115: 1743-55 (2005); Lin et al., Am J Pathol 173: 1617-27 (2008)). For whole mount LacZ staining, kidneys were dissected with a microtome (150 nm), then incubated in X-gal solution (pH7.5) 37C, 16 h, then post-fixed, as previously described (Duffield et al., J Clin Invest 115: 1743-55 (2005); Carroll et al., Dev Cell 9: 283-92 (2005)). In some cases tissues cryosectioned prior to staining (Humphreys et al., Cell Stem Cell 2: 284-91 (2008)), counterstained with nuclear fast red (Sigma) and dehydrated in alcohols and mounted with permount. For tissue sections X-gal staining, 4% PFA fixed cryosections were stained in X-gal solution (pH7.5) in coplin jars for 16 h, 37C, then washed X3 in PBS, post-fixed (5' 4% PFA on ice) prior to immunostaining. The following antibodies or lectins were used to detect tubule epithelial cells, macrophages, and myofibroblasts anti-α-SMA-Cy3, 1:400 (Sigma); F4/80, 1:200 (eBioscience) followed by anti-rat-Cy3 1:400 (Jackson), Lotus Lectin-FITC, 1:200 (Dako) antibodies and detected as previously described (Duffield et al., J Clin Invest 115: 1743-55 (2005); Lin et al., Am J Pathol 173: 1617-27 (2008)). Tubule injury score was determined by assessing PAS stained paraffin sections using a blinded scoring method. Images were captured by digital imaging (X200) sequentially over the entire sagittal section incorporating cortex and outer medulla (10-20 images). Each image was divided into 252 squares by a grid, and in each square the presence of tubule injury (tubule flattening, necrosis, apoptosis or presence of casts) resulted in a positive score. The final score is the percentage of squares with a positive score per image, averaged for all images from the individual kidney (20-40 images). TBM dissolution was scored blindly in digitally captured images (X400) acquired similarly to above from 20-40 sequential images. Images were divided by a 154 square grid. Proximal tubule containing squares were counted and the proportion of those squares containing dissolved TBM was counted and the accumulated totals for each image give a proportion which was the final score. Tubule dilatation was assessed morphometrically in whole sagittal sections (Duffield et al., J Immunol 177: 5902-11 (2006)). Ki67 staining was performed on cryosections using anti-Ki67-antibodies (1:200, clone SP6, Fisher), p-histone-H3 detected in cryosections using phospho-specific antibodies (1:800, sc-33361 Santa Cruz) and tubular basement membrane detected by anti-laminin antibodies (1:200 Sigma) all followed by anti-rabbit Cy3 antibodies (1:500 Jackson Immunoresearch). BrdU was detected in paraffin sections as previously described (Duffield et al., J Clin Invest 115: 56-65 (2005)), TUNEL was performed on paraffin sections using a kit from Roche. For quantification of αSMA and F4/80 by morphometry, DAB-immunostaining was performed on air-dried PLP-fixed cryosections, modified from previous studies (Lin et al., Am J Pathol 173: 1617-27 (2008); Duffield et al., J Clin Invest 115: 56-65 (2005)). αSMA which is also expressed by vascular smooth muscle was only quantified in kidney interstitium to avoid inclusion of arterioles. Morphometry was quantified using Fovea Pro software (Duffield et al., J Clin Invest 115: 56-65 (2005)). Manual counting of cells in tissue sections was carried out by blinded observation of X400 20-40 micrographs taken serially across sagittal sections of kidney. Positive Ki67 cells showed red nuclear staining, and TUNEL positive cells (expressed as number per 10 high power fields) showed brown stain in nuclei counterstained with hematoxylin that had characteristic nuclear morphology. Plasma Creatinine was assessed as previously described (Duffield et al., J Clin Invest 115: 1743-55 (2005)).

Injury-induced enhancement of the Wnt pathway response was noted. Control, BATgal negative mice did not show any staining 5 days after injury. Uninjured kidney from strain-matched, BATgal mice showed X-gal staining in a proportion of interstitial cells and tubule cells prominent in the papilla but the cortex and medulla showed almost no staining. By contrast, 5 days following injury there was marked upregulation of X-gal staining in both papilla and cortex. Similar injury-induced enhancement of the Wnt pathway response was noted in Axin2-lacz reporter mice and by detecting phosphorylation of the canonical pathway receptor Lrp6 (FIG. 1G) (Zeng et al., Nature 438(7069):873-877 (in eng) (2005))

Immuno-labelling of kidney sections from injured BATgal mice revealed that Lacz was detected in kidney epithelial cells (which double-labelled with lotus lectin) but was not detected in macrophages. In Axin2$^{+/LacZ}$ reporter mice a similar pattern of Wnt pathway responses was observed. Wild type mice and uninjured Axin2$^{+/Lacz}$ mice did not show any labelling whereas Axin2$^{+/LacZ}$ reporter mice showed labelling in epithelial cells and interstitial cells after injury. Double labelling of histological sections of injured kidney from Axin2$^{+/LacZ}$ mice for β-galactosidase and fibroblasts (αSMA) or macrophages (F4/80) confirmed that interstitial cells and epithelial cells but not macrophages showed a Wnt pathway response. The day 5-7 post-injury enhancement of the Wnt response suggested that the Wnt pathway could be a component of the injury repair mechanism.

To determine which Wnt pathway components might be important in the injury response, control and injured whole kidney were assessed for expression of mRNAs encoding ligands (Wnts), receptors (Fzds) and co-receptors (Lrp5 and 6). This showed that at the mid-point of the repair phase a number of ligands (Wnt2, 2b, 4, 5a, 7b, 10a) were up-regulated (FIGS. 1A-D). Though expression levels of receptors and co-receptors remained unchanged with injury (FIGS. 1A-D) Fzd4, Lrp5 and Lrp6 were prominently expressed (FIGS. 1A-1D). To further define the cell types responsible for expressing these ligands and receptors, kidney macrophages and proximal epithelial tubule cells (PTECs) were isolated using cell sorting methods (Lin et al., Am J Pathol 173(6):1617-1627 (2008)) and the same expression analysis was performed.

Single cells were prepared from blood and kidney as previously described (Lin et al., Am J Pathol 173: 1617-27 (2008)). Resuspended cells were added to tissue culture wells in complete DMEM/F12, and non-adherent cells washed after 1 h. Alternatively filtered single cells were resuspended in FACS buffer (PBS1.0% BSA), labeled with lotus lectin-FITC 1:200, or anti-CD45-PE, 1:200 (eBioscience), or anti-Kim-1-biotin-antibodies, 1:200 (RMT1-4, eBioscience) followed by streptavidin-APC (Jackson). Cells were sorted by FACSAria for Kim-1+, CD45− cells or LTL+, CD45− cells, lysed and RNA purified using RNA Easy (Qiagen) system. In other experiments filtered single cells from the kidney digest were labeled with antibodies against leukocyte CD45-FITC (1:200 EBioscience), neutrophils Ly6G-PE (1:200 Pharmingen) and myeloid cell CD11b-APC (1:200 EBioscience), and cells assessed for the proportion of Ly6G+ cells or the proportion of Ly6G−, CD11b+ cells to quantify macrophages.

Western Blotting was performed as follows. SDS page and blotting were carried out as previously described (Duffield et al., J Clin Invest 115: 1743-55 (2005); Duffield et al., J Immunol 164: 2110-9 (2000)). For detection of pLrp6, 60 μg of protein extracted from kidney cortex was applied to each lane. After blotting and blocking blots were incubated with anti-pLrp6 (1:500, Cell Signaling Technology) overnight, blots washed then incubated with anti-Rabbit-HRP antibodies (1:5000, Jackson Immunoresearch). After detection and stripping blots were re-detected with anti-beta-actin (1:1000, Santa Cruz Biotechnology).

Given the paucity of macrophages in healthy kidney, macrophages from the injured kidney were compared with autologous peripheral blood monocytes. Since Wnt reporter mice indicated that macrophages did not respond to the canonical Wnt pathway, we assessed only the expression of ligand genes. This showed that Wnt4, 7b, 10a and 10b were up-regulated (FIG. 1C). Wnt pathway reporter mice also indicated that PTECs were responding to the Wnt pathway during injury and so in this purified population, we assessed the expression of receptors. This showed that Fzd3, 4 and 7 were expressed at good levels in both control and injured kidney (FIG. 1A-D). Similarly, Lrp5 and 6 were expressed, but with little change in level in the injured tissue (FIG. 1A-D). These expression data are consistent with reporter mouse assessment suggesting that up-regulation of the canonical Wnt pathway is an injury-associated response and that macrophages may be a source of Wnt ligands to which epithelial cells respond.

Example 2

Inflammatory Macrophages Promote Kidney Repair and Show Enhanced Wnt Signalling Activity To test whether macrophages from the injured kidney showed enhanced Wnt signalling activity, macrophages were isolated 5 days after injury and co-cultured with the canonical Wnt reporter cell line, 'superTOPFLASH' (STF).

Bone marrow macrophages were prepared, cultured and used from d7-d10 (Duffield et al., J Immunol 164: 2110-9 (2010)). SuperTOPFLASH cells, were plated in 60 mm dishes and co-transfected with 0.6 μg Lrp5-flag, or 0.6 μg Lrp6, and 0.6 μg Fzd4, or 0.6 μg Fzd7 or 0.6 μg Fzd3, Fzd5, Fzd6, Fzd 8 and 2 μg pRL-TK renilla luciferase made up to 1.2 μg of total DNA with pcDNA3.1, using PEI transfection reagent using 1:4 ratio using methods modified those previously described (Boussif et al., Proc Natl Acad Sci USA 92: 7297-301 (2010)). After 48 h, cells were washed and transferred as responder cells to monocyte, BMMφ, or kidney Mφ cultures in 24 well plates in a 1:1 ratio and cultured in complete DMEM/F12. 24 h later, luciferase activity quantified using a dual luciferase reporter assay system (Promega) (Lobov et al., Nature 437: 417-21 (2005)). Relative Luciferase Activity (RLA) of firefly luciferase was normalized first for *Renilla* Luciferase, and then for monocyte co-culture or BM-Mφ co-culture. 293T cells were transfected with Wnt7b or empty vector using PEI complexes (1:4 ratio) and 48 h later 293T-Wnt7b cells were co-cultured with STF responder cells in a 1:1 ratio, and assessed for luciferase activity 24 h later. In other experiments additional 293T cells were transfected with Dkk1 or empty vector and co-cultured with 293T-Wnt7b and STF cells in a 1:1:1 ratio. In other experiments, filtered 24 h conditioned medium from 293T-Dkk1 cells or 293T-empty vector was transferred to 293T-Wnt7b co-cultured with STF cells. In other experiments primary BM derived Mφs were retrovirally transduced to express Wnt7b using amphotropic retrovirus (see above). Expression of Wnt7b was confirmed by RT-PCR (not shown). On d7 of BMMφ culture, STF reporter cells were transferred to BMMφ-Wnt7bIRESGFP or BMMφ-GFP in a 1:1 ratio and cultured for 24 h prior to assessing for luciferase activity.

Compared with control autologous monocytes (FIG. 2A, PBM) or bone marrow macrophages (Table 1), post-injury macrophages induced a three-fold increase in canonical Wnt signalling via Lrp5 with Fzd3, 4, or 7 and a five-six fold increase via Lrp6 with Fzd3, 4, or 7 (FIG. 2B). Despite the expression of Wnt2, 2b, 5a, 5b in monocytes and Wnt2, 3, 5a, 5b by unactivated cultured bone marrow (BM) macrophages, no signalling was identified from these leukocytes to STF cells (Table 1 and FIG. 2J) indicating that macrophage expression alone of Wnt2, 2a 5a, 5b, does not equate with canonical Wnt responses in neighbouring cells, and therefore that not all Wnts are able to actively engage paracrine signalling. Addition of the Wnt pathway inhibitor Dkk1 in recombinant form (FIG. 2C) or co-transfection of Dkk1 in STF reporter cells significantly suppressed kidney macrophage-stimulated Wnt signalling. The Fzd, Lrp5/6 and Dkk1-dependence of the STF response to macrophages demonstrates that this is a canonical Wnt pathway response. Furthermore, these data show that the Wnt receptors and co-receptors expressed by kidney epithelium can mediate responses to the Wnt activities produced by macrophages from the injured kidney.

TABLE 1 absolute light units from cultures of STF cells transfected to express Renilla luciferase and a combination of Wnt receptors additionally, and co-cultured with no cells, d 7 BM Mφs, or purified d 7 post injury kidney macrophages.

| STF cells with receptors | Co-culture cell | Firefly Luciferase | Renilla Luciferase |
|---|---|---|---|
| No receptors | No cell | 396 | 60 |
| | BM Mφ | 418 | 54 |
| | d 7 injury kidney Mφ | 770 | 58 |
| Lrp5 + Fzd4 | No cell | 6859 | 311 |
| | BM Mφ | 4231 | 196 |
| | d 7 injury kidney Mφ | 8225 | 312 |
| Lrp5 + Fzd7 | No cell | 14472 | 218 |
| | BM Mφ | 12073 | 256 |
| | d 7 injury kidney Mφ | 29691 | 328 |
| Lrp66 + Fzd4 | No cell | 436 | 83 |
| | BM Mφ | 311 | 88 |
| | d 7 injury kidney Mφ | 2231 | 79 |
| Lrp6 + Fzd7 | No cell | 401 | 92 |
| | BM Mφ | 535 | 232 |
| | d 7 injury kidney Mφ | 1692 | 108 |

Wnt7b has been identified as a macrophage-expressed ligand (FIG. 1A-D, FIG. 2J and ref Lobov I B, et al., Nature 437(7057):417-421 (2005)). To assess whether this ligand was capable of inducing a response via Fzd4 and 7 with Lrp5 or 6, Wnt7b was stably expressed by retroviral-transduction in a cell line and also primary, bone marrow-derived macrophages. These macrophages were used for STF cell co-culture at day 7 after marrow harvest when they do not normally express endogenous Wnt7b. Wnt7b expressing BM macrophages induced a Wnt pathway response with all receptor/co-receptor combinations with Fzd4/Lrp6 showing the greatest response (FIG. 2D and Table 2). As with freshly isolated macrophages from the injured kidney, Dkk1 could suppress the signalling (FIG. 2D). These data further support the notion that macrophages could be a source of Wnt ligand activity in the injured kidney. Furthermore, activation of BM macrophages cultured on glass with $(Kdo)_2$-lipidA, a selective Toll-like receptor 4 agonist, lead to robust induction of Wnt7b (FIG. 2J), confirming that Wnt7b is an inducible ligand of the activated macrophage.

TABLE 2 absolute light units from cultures of STF cells transfected to express Renilla luciferase and a combination of Wnt receptors additionally, and co-cultured with control 293 cells, or 293 cells stably expressing Wnt7b.

| STF cells with receptors | Co-culture cell | Firefly Luciferase | Renilla Luciferase |
|---|---|---|---|
| No receptors | 293-control | 331 | 58 |
| | 293-Wnt7b | 6636 | 64 |
| Lrp5 + Fzd4 | 293-control | 6430 | 171 |
| | 293-Wnt7b | 26891 | 208 |
| Lrp5 + Fzd7 | 293-control | 16172 | 204 |
| | 293-Wnt7b | 51628 | 310 |
| Lrp66 + Fzd4 | 293-control | 573 | 88 |
| | 293-Wnt7b | 10057 | 104 |
| Lrp6 + Fzd7 | 293-control | 464 | 82 |
| | 293-Wnt7b | 11538 | 96 |

As described above, after injury to the kidney there is a defined phase of repair that begins on day 2 (Duffield et al., J Clin Invest 115(7):1743-1755 (2005); Humphreys et al., Cell Stem Cell 2(3):284-291 (2008); Duffield et al., J Immunol 177(9):5902-5911 (2006)). Since the repair phase correlates with macrophage numbers (FIGS. 1E-F) we reasoned that that macrophage Wnt ligands might be involved in repair and we tested this by performing macrophage ablation experiments in vivo. To test the possibility that kidney macrophages stimulated Wnt pathway responses during injury, mice with the CDJJb-DTR allele that allows conditional ablation of macrophages in vivo (Duffield et al., J Clin Invest 115(1):56-65 (2005)) were cross-bred with the Wnt reporter $Axin2^{LacZ}$ mice and screened the F1 progeny for the presence of the LacZ allele and CD11b-DTR transgene. Reporter expression was assessed after injury with or without macrophage ablation.

Diphtheria toxin (DT) was injected to ablate macrophages on days 3 to 6 after injury, as this corresponds to the repair phase. Macrophage ablation was first confirmed by histological assessment of macrophage numbers using F4/80 labelling and performed morphometric measurements of the F4/80-positive area in experimental and control mice (FIG. 2E). This showed, as expected (Duffield et al., Am J Pathol 167(5):1207-1219 (2005)), that at least 80% of macrophages in the injured kidney could be ablated by DT injection (FIG. 2E). Morphometric measurements showed that with or without DT, uninjured kidney cortex and medulla had limited X-gal positive area (FIG. 2F, CON) and that as expected, injury increased the X-gal positive area dramatically (FIG. 1G, FIG. 2F, I/R, white bar), similar to findings in BAT-gal mice. Importantly, the application of DT and the accompanying macrophage ablation resulted in a dramatic reduction of X-gal staining in all areas of medulla and cortex of CD11b-DTR; $Axin2^{LacZ}$ kidneys (FIG. 2F, I/R, black bar). These data suggested that macrophages were a major source of stimulus of Wnt responses in kidney epithelium during injury. In addition to reducing expression of the Wnt reporter, macrophage ablation resulted in a striking failure of normal regeneration of kidney tubule epithelium (FIGS. 2G and 2K) and as indicated by an injury score that was approximately doubled in the absence of macrophages (FIG. 2G). Furthermore, when macrophages were ablated there was failure of normal functional recovery of the kidneys as measured by plasma creatinine (FIG. 2H).

Example 3

Genetic Disruption of Wnt Responses in the Kidney Prevents Normal Repair

Proximal tubule epithelial cells express a limited set of Wnt pathway receptors including Fzd4 (FIGS. 1A-D). To confirm the expression pattern of Fzd4, kidney sections from $Fzd4^{+/lacz}$ mice were stained with X-gal and with antibodies to F4/80. The results confirmed that Fzd4 expression was restricted to epithelial cells and not macrophages. To test whether Fzd4 was required for the injury response, kidney ischemia reperfusion injury experiments were performed in $Fzd4^{LacZ/LacZ}$ mutant mice and compared the regeneration response with $Fzd4^{+/+}$ littermate controls. $Fzd4^{LacZ/LacZ}$ mice show reduced growth and have abnormalities of capillary development in the eye and cerebellum (Xu et al., Cell 116 (6):883-895 (2004)) (genotyping of the $Fzd4^{LacZ/LacZ}$ mice was performed with the following primer pairs: WT allele; 5'-CACACGTGGCAAAAGTGTTG-3' (SEQ ID NO:6), 5'-CAGTTGAAATCCCACCCAGT-3' (SEQ ID NO:7);

Mutant allele: 5'-TGTCTGCTAGATCAGCCTCT-3' (SEQ ID NO:8), 5'-CATCAACATTAAATGTGAGCGAGT-3' (SEQ ID NO:9).) However, their kidneys are developmentally normal. In response to kidney injury, Fzd4$^{LacZ/LacZ}$ mice showed a normal influx of myofibroblasts (FIG. 3A) and macrophages (FIG. 3B). Furthermore, there was no significant difference in the proliferation response as determined by the pan cell cycle marker Ki67 (FIG. 3C). By contrast, Fzd4$^{lacZ/lacZ}$ mice showed a modest but statistically significant persistent injury according to PAS staining (FIG. 3D) and this was accompanied by increased epithelial cell apoptosis (FIG. 3E). These data indicate that Fzd4-dependent responses in kidney epithelial cells are required for repair of injury.

With robust Lrp5 and Lrp6 expression in proximal tubule epithelial cells, it was theorised that mutation of these co-receptors might, like Fzd4 mutation, compromise kidney repair and regeneration. Lrp5$^{+/LacZ}$ and Lrp6$^{+/LacZ}$ mice (C57BL6) were generated as previously described (Lobov IB, et al., Nature 437(7057):417-421(2005)) and genotyped with the following primer sets: Lrp5: (1)5'-GGCTCGGAG-GACAGACCTGAG-3' (SEQ ID NO:10), (2) 5'-CTGT-CAGTGCCTGTATCTGTCC-3' (SEQ ID NO:11), (3) 5'TCCAAGCGGCTTCGGCCAG-3' (SEQ ID NO:12). LRP6: (1) 5'-CAGGCATGTAGCCCTTGGAG-3' (SEQ ID NO:13), (2) 5'-ACTACAAGCCCTGCACTGCC-3' (SEQ ID NO:14), (3) 5'-GTAGAGTTCCCAGGAGGAGCC-3' (SEQ ID NO:15). Homozygosity for both Lrp5 and Lrp6 null mutations results in early embryonic lethality but double heterozygote mice survive to adulthood (Glass et al., Dev Cell 8(5): 751-764 (2005); Holmen et al., J Bone Miner Res 19(12): 2033-2040 (2004); Kato et al., J Cell Biol 157(2):303-314 (2002)). When analyzed after kidney injury, Lrp5$^{+/LacZ}$; Lrp6$^{+/Lacz}$ mice exhibited increased tubule injury early in the repair process at day 2 (FIG. 3F). Furthermore, there was a persistence of epithelial injury after seven days (FIG. 3G). According to F4/80 labelling there was no difference in macrophage recruitment observed at day 7 (FIG. 3G) and no change in the total number of kidney cells in the cell cycle (Ki67 positive) at day 2 (FIG. 3F) or 7 (FIG. 3G). However, there was a quantifiable increase in apoptotic tubule cells at day 7 (FIG. 3G) and increased numbers of interstitial myofibroblasts (FIG. 3G). These changes are consistent with those observed when macrophages are ablated or when Fzd4 is mutated (as described herein). These data strengthen the case for canonical Wnt pathway-dependent repair and regeneration in kidney epithelium.

Example 4

Macrophage Wnt7b Promotes Regeneration by Directing

To assess the role of Wnt7b in macrophages specifically in vivo the Wnt7b$^{C3}$ loxP conditional allele (FIG. 4A) was used in combination with the monocyte-macrophage specific Csf1R-icre transgene (FIG. 4A) (Deng et al., Am. J. Patho. 176(2):952-67 (2010); Lin et al., J Immunol. 183(10):6733-43 (2009)). The floxed conditional Wnt7b$^{C3}$ allele was generated as previously described (Rajagopal et al., Development 135(9):1625-1634 (2008)). Mice heterozygous for the Wnt7b$^{C3}$ allele (C57BL6) were crossed with germline Cre mice (Lakso et al., Proc Natl Acad Sci U S A 89(14):6232-6236 (1992)), or strain matched controls, to generate heterozygous mutants (Wnt7b+/−). Genotyping for the presence of the Wnt7b$^{C3}$ allele was performed with 5'-GTCTCTGTC-CTTAGTTGGGTC-3' (SEQ ID NO:16), 5'-CCAGAGAC-CAGTACACCTGAG-3' (SEQ ID NO:17) primers. Mutants backcrossed with Wnt7b$^{C3/C3}$ mice, and the offspring were crossed with Csf1R-iCre transgenic mice resulting in Csf1R-iCre; Wnt7b$^{C3}$ experimental mice, and Wnt7b$^{C3/-}$ and Csf1R-iCre; Wnt7b$^{C3/+}$ controls. Presence of the Wnt7b conditional allele or WT allele was confirmed using the following primers 5' -TGACAGAGGATGGGGAGAAG-3' (SEQ ID NO:18), 5' -GGTCTTTCCAAGGGTGGTCT -3' (SEQ ID NO:19). Transgenic Csf1R-iCre mice (Balb/c background) were generated (23) and genotyping was performed using the following primers 5'-CTAATCGCCATCTTCCAGCAGG-3' (SEQ ID NO:20), 5'-GCTAAGTGCCTTCTCTACACCT-3' (SEQ ID NO:21).

Exon 3 deletion specifically in macrophages was confirmed (FIG. 4B). The fact that no C3 allele was detected by PCR of genomic DNA from macrophages indicates that in the experimental mice there was complete deletion of Wnt7b. Injury of the kidneys was performed in these mice and control mice and repair assessed at day 7. Strikingly, while repair of the injured epithelium proceeded as expected in littermate control Wnt7b$^{C3/-}$ and Csf1R-icre; Wnt7b$^{C3/+}$ mice, repair was substantially retarded in Csf1R-icre; Wnt7b$^{C3/-}$ experimental mice (FIGS. 4C and 4K-L). For detection of Kim1, Western blotting was performed as described above, with 50 µg of whole kidney protein lysate applied to each lane. Blots were incubated with anti-Kim1 antibodies (1:1000, EBioscience) overnight, blots washed then incubated with anti-rat-HRP antibodies (1:5000, Jackson Immunoresearch). After detection and stripping blots were re-detected with anti-beta-actin (1:1000, Santa Cruz Biotechnology). This was evident from epithelial injury scores, assessed by blinded morphometry, that showed severe persistent epithelial injury in the homozygous somatic mutant (FIG. 4C). In addition, the PTEC-specific marker expressed only by injured, dedifferentiated epithelial cells, Kidney Injury Molecule-1 (Kim1) (Ichimura et al., J Clin Invest 118(5):1657-1668 (2008)), was highly expressed in kidney cortex from experimental mice lacking Wnt7b in macrophages 7d after injury, whereas in control mice the level of Kim1 was lower (See FIG. 4K-L). Macrophage recruitment to the kidneys (FIG. 4D) and the proportion of epithelial cells in the cell cycle (FIG. 4E) were not significantly changed but there were significant increases in interstitial fibrosis according to collagen labelling (FIG. 4F) and in apoptotic epithelial cells (FIG. 4G). These data provide strong evidence that the macrophage is a source of Wnt7b that is required for repair and regeneration in the injured kidney.

To understand the mechanisms of Wnt7b-mediated repair, tubule basement membrane (TBM) integrity was scored blindly for dissolution (See FIG. 4H). Strikingly Csf1R-icre; Wnt7b$^{C3/-}$ experimental mice had increases in TBM dissolution indicating Wnt7b responses in epithelial cells promote TBM repair. To explore the function of Wnt7b in epithelial cell-cycle progression, G1/S-phase in epithelial cells was identified by BrdU uptake and G2/M by phosphorylation of Histone-H3 (See SI Text and FIG. 4M-O) (Cude et al., J Cell Biol 177(2):253-264 (2007)). Although entry into cell cycle, detected by BrdU, was unaffected by loss of macrophage Wnt7b in Csf1R-icre; Wnt7b$^{C3/C3}$ experimental mice, progression through G2 was suppressed since there was a doubling of epithelial cells expressing pHistone-H3 in the absence of mitosis in experimental mice. This suggests that Wnt7b responses drive epithelial cells through a G2 checkpoint thereby avoiding apoptotic cell death. Wnt7b responses in epithelial cells trigger both basement membrane regeneration, and repopulation of the tubule by overcoming a G2 arrest in the cell cycle. Extracellular matrix genes such as fibronectin and laminin, and cell cycle progression genes such as n-myc and c-jun have been reported to be directly regulated by the Wnt pathway suggesting that the mechanisms of epithelial repair described here may be a direct consequence of epithelial Wnt responses (Dickinson and Sive, Development 136(7):1071-1081 (2009)).

Example 5

Dickkopf-2 Promotes Kidney Epithelial Repair

The data presented thus far argue that enhancement of Wnt signalling might provide some therapeutic benefit for damaged kidneys by accelerating the regeneration of tubule epithelium. The Dickkopf family of proteins are soluble Wnt modulators. Dkk2 binds to Lrp5 or Lrp6 on the cell-surface and can enhance signalling. This enhancement is negatively regulated by the presence of the transmembrane protein Kremen (Mao et al., Nature 417(6889):664-667 (2002); Mao and Niehrs, Gene 302 (1-2): 179-183 (2003)).

The C2 cysteine-rich domain of Dkk2 that retains functional activity (See FIG. 5A) was cloned, expressed and purified in quantity as follows. Total RNA was generated from tissue and cells using RNA Easy kit, cDNAs generated from 1 µg of total RNA using iScript. Individual PCRs for Wnt pathway components were performed using optimized primers and conditions (see Table 3). The ORF for Wnt7b and Dkk1 was cloned from C57BL6 d7 ureteral obstruction kidney cDNA, into pGEM-Teasy and subcloned into MSCV-IRES-GFP, EGFPN1, pLVPT-tTR-KRAB. Lrp-5 and Lrp-6 were cloned into pcDNA3.1 v5/his with a stop codon at the end of the ORF. Fzds3-8 were cloned into pRK5-IgG. The primer pairs shown in Table 3 were used to amplify message for Dkk1 with the indicated annealing temperature. The extension time was 60 s and the number of cycles was optimized for each product. In each case specificity of product was confirmed by nested PCR or by sequencing of PCR products.

TABLE 3

| PCR Primers and Conditions for Wnt Pathway Components | | | | |
|---|---|---|---|---|
| Gene | Primer 1 | SEQ ID NO: | Primer 2 | SEQ ID NO: |
| The following primer pairs were used with annealing temperature of 52° C.: | | | | |
| Dkk1 | 5'-CTC TCg gCT ggT AgT CCT TgA A-3' | 22 | 5'-TAA gTT ggC Agg CTT CCT TCT g-3'. | 23 |
| The following primer pairs were used with annealing temperature of 50° C.: | | | | |
| Wnt1 | 5'-CTC ATg AAC CTT CAC AAC AAC g-3' | 24 | 5'-CAg CAC AgC AgC TCA CAg C-3' | 25 |
| Wnt2 | 5'-Cgg CCT TTg TTT ACg CCA TC-3' | 26 | 5'-TgT CCT Tgg CAC TTC CTT TC-3' | 27 |
| Wnt2b | 5'-Tgg AgA gCA CTC TCA gAC TTC C-3' | 28 | 5'-ACA gTg TTT CTg CAC TCC TTg C-3' | 29 |
| Wnt3 | 5'-gTA AAT gCC ACg GGT TgT CC-3' | 30 | 5'-CTC CgT CCT CgT gTT gTg g-3' | 31 |
| Wnt4 | 5'-AAC ATC gCC TAT ggC gTA gC-3' | 32 | 5'-CAC CgT CAA ACT TCT CCT TTA gC-3' | 33 |
| Wnt6 | 5'-TAC CAg CAT CTg CAg gAA gg-3' | 34 | 5'-gAC TTC TCA TCC CCg AAg TCC-3' | 35 |
| Wnt7a | 5'-gAC gCC ATC ATC gTC ATA gg-3' | 36 | 5'-ATg TTC TCC TCC Agg ATC TTC-3' | 37 |
| Wnt7b | 5'-AAg AAC TCC gAg TAg ggA gTC g-3' | 38 | 5'-TgC gTT gTA CTT CTC CTT gAg C-3' | 39 |
| Wnt9a | 5'-CCT gAC TAT CCT CCC TCT gAC C-3' | 40 | 5'-gCT gCT gTA CTT gAg gTT gTC C-3' | 41 |
| Wnt9b | 5'-gTA CAg CAC CAA gTT CCT CAg C-3' | 42 | 5'-ACT ggA gTC TCg AgA ACA CAC C-3' | 43 |
| Wnt10a | 5'-gAA CAA AgT CCC CTA CgA gAg C-3' | 44 | 5'-ggT TgT TgT ggA gTC TCA TTC g-3' | 45 |
| Wnt10b | 5'-gTg gTA ACg gAA AAC CTg AAg C-3' | 46 | 5'-CTC ATC ACA CAg CAC ATA ACA gC-3' | 47 |
| Wnt16 | 5'-gCC ATg AAT CTA CAC AAC AAC g-3' | 48 | 5'-CTg ACT ACA Tgg gTg TTg TAg CC-3' | 49 |
| GAPDH | 5'-ACT CCA CTC ACg gCA AAT TC-3' | 50 | 5'-CAC ATT ggg ggT Agg AAC AC-3' | 51 |
| Lrp5 | 5'-AAg ACC CTg CTT gAg gAC AA-3' | 52 | 5'-gAg Tgg GAT AgC CAC ATC gT-3' | 53 |

TABLE 3-continued

PCR Primers and Conditions for Wnt Pathway Components

| Gene | Primer 1 | SEQ ID NO: | Primer 2 | SEQ ID NO: |
|---|---|---|---|---|
| Lrp6 | 5'-gAg CTC ATC ggT GAC ATg AA-3' | 54 | 5'-gCT CgA ggA CTg TCA Agg TC-3' | 55 |
| Kremen1 | 5'-ggA gAT CCT CCC Agg AAA Ag-3' | 56 | 5'-ggA gCA gCA gCT AgA ggA gA-3'. | 57 |
| Kremen2 | 5'-CAg AAg ATC ggA CAG gAA gC-3' | 58 | 5'-CAG AAA TCC TCC TGA CTC TG-3' | 59 |

The following primer pairs were used with annealing temperature of 49° C.:

| Fzd3 | 5'-gCg gTT gAT ggA gTT gCT AT-3' | 60 | 5'-AAg gCA AAT CTT ggC ACA TC-3' | 61 |
| Fzd4 | 5'-gCT ACA ACg TgA CCA AgA TgC-3' | 62 | 5'-CAA ACC CAA ATT CTC TCA ggA C-3' | 63 |
| Fzd5, | 5'-CCT ggT ggA gAg Tgg TgA TT-3' | 64 | 5'-CAg TAA Tgg CCC CAC ACT CT-3' | 65 |
| Fzd6 | 5'-AAg TCC ATg ggA ACT AgC ACA g-3' | 66 | 5'-TCT TTC CTA gCT CTg gAA gCT g-3' | 67 |
| Fzd7 | 5'-TgT ggT CAg TgC TgT gCT g-3' | 68 | 5'-CAC TgA gTA ggT CAC CAT CCA C-3' | 69 |
| Fzd8 | 5'-ATA Tgg AgC gCT TTA AGT ACC C-3' | 70 | 5'-CAC CgC gAT ggA CTT gAC-3' | 71 |

The following primer pairs were used with an annealing temperature of 48° C.:

| Wnt3a | 5'-ACC CCA gTA CTC CTC TCT gAg C-3' | 72 | 5'-CAT TCC TCC AAA TTC AAT gTC C-3' | 73 |
| Wnt8 | 5'-GCA TgC TTT TCA gTT TTC AAC C-3' | 74 | 5'-CCT TTA ggT AAT TTC CCA TCT gC-3' | 75 |

The following primer pairs were used with an annealing temperature of 45° C.:

| Wnt5a | 5'-ggC CAT AAT CTT gTg TTA gC-3' | 76 | 5'-ATA ggA AAA gCA CAA ATg gA-3' | 77 |
| Wnt5b | 5'-Tgg ATg gAT ggA TgA TAg AT-3' | 78 | 5'-TCC TgC AgT gTg TAC TCA gA-3' | 79 |
| SFRP1 | 5'-TgT TCg ggA CAT CAT TAC CA-3' | 80 | 5'-gCC CAC gTA CCT CCT TCA TA-3' | 81 |
| SFRP2 | 5'-CgA CAT CAT ggA AAC CCT TT-3' | 82 | 5'-ggA gCg gAA gTg TAC Ag-3' | 83 |
| SFRP3 | 5'-TTA CTT CCg gTC CCC TTT CT-3' | 84 | 5'-TTC CTg gTg TTg ggC TAC TC-3' | 85 |
| SFRP4 | 5'-TCC CTC TCA TCA CCA ATT CC-3' | 86 | 5'-gCA gCA CCA CCT TAT CCT gT-3' | 87 |
| SFRP5 | 5'-CAC TTg gCC TCA CCT TCA CT-3' | 88 | 5'-gCC TTg gAT CTT gCT CTT Tg-3'. | 89 |

To generate the retrovirus, 293T17 cells were cultured in 100 mm dishes at 50% confluence, cotransfected with MSCV-Wnt7b-IRES-GFP or MSCV-IRES-GFP and pCLAmpho (Imgenex) in equal molar ratio using PEI complexes (1:4 ratio). After 16 hours, virus was collected in 6 ml of macrophage medium or other cell culture medium for 6 or 24 h, filtered through a 0.45 μm filter. For macrophage retroviral transduction, bone marrow cells were cultured for 3d in macrophage medium then cultured in retrovirus-conditioned-macrophage-medium containing polybrene (14 μg/ml) for 16 hours, washed, then cultured until day 7. 293T cells were cultured with retrovirus-conditioned-medium (24 h conditioning) containing polybrene (8 μg/ml) for 24 h. A further 24 h later cells were treated with puromycin 3 μg/ml for 72 h.

The recombinant protein Dkk2C (amino acids Met172-Ile259 of mouse Dkk2 (SEQ ID NO:91) was expressed and purified from an Escherichia coli system as described previously (Chen et al., J Biol Cherm 283: 23364-70 (2008)). The recombinant protein contains an N-terminal S tag and a thrombin cleavage site between the S tag and Dkk2C to enable purification. For detection of Dkk2-C2, western blots of 50μg of whole kidney protein lysate per lane were incubated with anti-S-tag antibodies (1:500, BD Biosciences) followed by secondary HRP conjugated antibodies. After detection and stripping blots were re-detected with anti-beta-actin (1:1000, Santa Cruz Biotechnology). The purified recombinant Dkk2C contained only one single band in SDS-PAGE.

This C2 recombinant form of Dkk2 was administered from d0 to WT mice that were uninjured or which had kidney injury. Kidneys were harvested on day 2 and day 7 after injury and assessed quantitatively for injury. For detection of Dkk2-C2, Western blots of 50 µg of whole kidney protein lysate per lane were incubated with anti-5-tag antibodies (1:500, BD Biosciences) followed by secondary HRP conjugated antibodies. After detection and stripping blots were re-detected with anti-beta-actin (1:1000, Santa Cruz Biotechnology). At both time points tubule injury scores were more severe in vehicle treated mice (FIGS. 5B-C, 5G). Dkk2 administration (at either 3 nmoles/g body weight or 210 ng/g body weight) had no effect on macrophage recruitment at day 7 post-FR (FIG. 5C) but there were fewer TUNEL-positive apoptotic tubule epithelial cells (FIG. 5C, 5G) with no significant change in epithelial cells in cell cycle (FIG. 5C, 5G). Mice with sham surgery remained well with normal body weight and activity, suggesting that systemic Dkk2 had no systemic deleterious effects. When systemic delivery of Dkk2 was delayed until after peak injury at d1, it was nevertheless detectable in the kidney (FIG. 5G) and it retained the capacity to improve kidney function as assessed by plasma creatinine levels (FIG. 5D). This underscores a primary role for Dkk2 in repair of the kidney. Dkk2 can either augment or inhibit Wnt responses depending on the expression of Kremen proteins. To understand whether Dkk2 was functioning to augment the canonical pathway, Wnt signalling in kidney cortex of d5 post I/R mice was assessed by detection of phosphorylated Lrp6 since canonical signalling requires phosphorylation of this co-receptor (Zeng et al., Nature 438(7069):873-877 (in eng) (2005)) (FIG. 5E). pLrp6 was not detected in healthy adult kidney cortex (FIG. 1G) but was robustly detected in kidney cortex following injury. Therapy with Dkk2-C2 resulted in enhanced pLrp6 detection in the kidney cortex at d5 post I/R (FIG. 5E). Therefore Dkk2 functions to enhance canonical Wnt responses in regenerating kidney cortex. Since Dkk2 function depends transcripts of Kremen1 and 2 were expressed at very low levels by the Wnt receptive kidney epithelial cells (FIG. 5F). Collectively, these observations as consistent with the major role for Dkk2-C2 an enhancer of endogenous Wnt responses.

Example 6

Macrophages Regulate Pancreatitis Severity During Both Injury and Repair

Two recent studies have shown roles for macrophages in repair of skeletal muscle (Arnold et al., J Exp Med 204(5): 1057-1069 (2007)) and the heart (Nahrendorf M, et al., J Exp Med 204(12):3037-3047 (2007)). It was hypothesized that macrophages function in all organs to promote repair after injury, perhaps by recapitulating developmental pathways in addition to clearing debris. To test this hypothesis further injury was induced in the pancreas using two different models of acute pancreatitis that closely mimic human disease, the caerulein model of secretagogue pancreatitis and the sodium taurocholate pancreatic duct injection model of bile reflux pancreatitis. Similar to the kidney, many macrophages are present in the pancreas during the repair phase. Many monocytes are recruited to the kidney early after injury (FIG. 6A). Using CD11b-DTR mice, monocytes and macrophages were first ablated with DT injection, then caerulein pancreatitis was induced. The results indicated that macrophage ablation at the time of induction of disease markedly attenuates disease (FIG. 7B) as assessed by quantification of edema, injury score, inflammation assessment, plasma amylase. Next, disease was induced and normal recovery permitted to occur (which starts functionally after 24 h and continues for 7-14 days). Macrophages were depleted using a single injection of DT from 24 h after peak injury and assessed the pancreas on d7. The persistence of injury of the pancreas can be measured by quantification of edema, injury score, inflammation assessment, plasma amylase (FIG. 7B), but in addition there is acquisition of fibrosis in the pancreas in response to injury that normally resolves (FIG. 7C-D). Macrophage ablation during recovery resulted in persistent edema, persistent elevation of amylase (FIG. 7E), and a failure of resolution of fibrosis. In addition, an epithelial injury score indicated the exocrine epithelial cells were unable to regenerate normally in the absence of recruited macrophages (FIG. 7E). These data strongly suggest that macrophages have a critical role in repair of many organs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for enhancing tissue repair and regeneration following injury in a kidney or pancreas, the method comprising administering a therapeutically effective amount of a composition comprising an agent that enhances canonical Wnt signaling, wherein the agent is selected from the group consisting of human Dikkopf 2 (Dkk2), mouse DKK2, an active fragment of mouse Dkk2 comprising SEQ ID NO: 91, and an active fragment of human Dkk2 comprising SEQ ID NO:90, and wherein the tissue repair and regeneration following injury in a kidney or pancreas is enhanced.

2. The method of claim 1, wherein the injury is an injury in which activated macrophages play a role in recovery.

3. The method of claim 2, wherein the injury is an ischemic injury.

4. The method of claim 1, wherein the composition enhances regeneration of epithelial cells.

5. The method of claim 1, wherein the composition enhances regeneration of vasculature in the kidney.

6. The method of claim 1, wherein the composition is administered systemically or by infusion through the vasculature.

7. The method of claim 1, wherein the composition enhances LRP5/6 or Fzd 4/7/8 activity in epithelial cells.

8. The method of claim 1, wherein the human DKK2 comprises SEQ ID NO:92.

9. The method of claim 1, wherein the mouse DKK2 comprises SEQ ID NO:93.

10. The method of claim 2, wherein the injury is an inflammatory injury.

11. The method of claim 2, wherein the injury is a toxic injury.

12. The method of claim 2, wherein the injury is an infectious injury.

13. The method of claim 2, wherein the injury is an autoimmune injury.

14. The method of claim 1, wherein the composition enhances regeneration of vasculature in the pancreas.

15. A method for enhancing tissue repair and regeneration following injury in a kidney, the method comprising administering a therapeutically effective amount of a composition comprising an active fragment of human Dkk2 comprising SEQ ID NO:90, and wherein the tissue repair and regeneration following injury in a kidney is enhanced.

16. A method for enhancing tissue repair and regeneration following injury in a pancreas, the method comprising administering a therapeutically effective amount of a composition comprising an active fragment of human Dkk2 comprising SEQ ID NO:90, and wherein the tissue repair and regeneration following injury in a pancreas is enhanced.

* * * * *

SEQUENCE LISTING

```
<160> NUMBER OF SEQ ID NOS: 93

<210> SEQ ID NO 1
<211> LENGTH: 11
<212> TYPE: PRT
<213> ORGANISM: Artificial Sequence
<220> FEATURE:
<223> OTHER INFORMATION: synthetically generated peptide

<400> SEQUENCE: 1

Lys Glu Ala Pro Pro Ala Pro Pro Gln Ser Pro
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: synthetically generated peptide
```

-continued

<400> SEQUENCE: 2

Gly Lys Glu Ala Pro Pro Ala Pro Pro Gln Ser Pro
 1               5                   10

<210> SEQ ID NO 3
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 3
agtccatctt cattccgcct agc                                    23

<210> SEQ ID NO 4
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 4
tggtaatgct gcagtggctt g                                      21

<210> SEQ ID NO 5
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 5
aagctgcgtc ggatacttga ga                                     22

<210> SEQ ID NO 6
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 6
cacacgtggc aaaagtgttg                                        20

<210> SEQ ID NO 7
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 7
cagttgaaat cccacccagt                                        20

<210> SEQ ID NO 8
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 8
tgtctgctag atcagcctct                                        20

<210> SEQ ID NO 9

```
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 9
catcaacatt aaatgtgagc gagt                                            24

<210> SEQ ID NO 10
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 10
ggctcggagg acagacctga g                                               21

<210> SEQ ID NO 11
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 11
ctgtcagtgc ctgtatctgt cc                                              22

<210> SEQ ID NO 12
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 12
tccaagcggc ttcggccag                                                  19

<210> SEQ ID NO 13
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 13
caggcatgta gcccttggag                                                 20

<210> SEQ ID NO 14
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 14
actacaagcc ctgcactgcc                                                 20

<210> SEQ ID NO 15
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 15
```

```
gtctctgtcc ttagttgggt c                                              21
```

<210> SEQ ID NO 16
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 16

```
gtctctgtcc ttagttgggt c                                              21
```

<210> SEQ ID NO 17
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 17

```
ccagagacca gtacacctga g                                              21
```

<210> SEQ ID NO 18
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 18

```
tgacagagga tggggagaag                                                20
```

<210> SEQ ID NO 19
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 19

```
ggtctttcca agggtggtct                                                20
```

<210> SEQ ID NO 20
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 20

```
ctaatcgcca tcttccagca gg                                             22
```

<210> SEQ ID NO 21
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 21

```
gctaagtgcc ttctctacac ct                                             22
```

<210> SEQ ID NO 22
<211> LENGTH: 22
<212> TYPE: DNA
<213> ORGANISM: Artificial Sequence
<220> FEATURE:

<223> OTHER INFORMATION: synthetically generated oligonucleotide

<400> SEQUENCE: 22
ctctcggctg gtagtccttg aa                                              22

<210> SEQ ID NO 23
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 23
taagttggca ggcttccttc tg                                              22

<210> SEQ ID NO 24
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 24
ctcatgaacc ttcacaacaa cg                                              22

<210> SEQ ID NO 25
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 25
cagcacagca gctcacagc                                                  19

<210> SEQ ID NO 26
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 26
cggcctttgt ttacgccatc                                                 20

<210> SEQ ID NO 27
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 27
tgtccttggc acttcctttc                                                 20

<210> SEQ ID NO 28
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 28
tggagagcac tctcagactt c                                               21

<210> SEQ ID NO 29

```
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 29
acagtgtttc tgcactcctt gc                                              22

<210> SEQ ID NO 30
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 30
gtaaatgcca cgggttgtcc                                                 20

<210> SEQ ID NO 31
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 31
ctccgtcctc gtgttgtgg                                                  19

<210> SEQ ID NO 32
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 32
aacatcgcct atggcgtagc                                                 20

<210> SEQ ID NO 33
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 33
caccgtcaaa cttctccttt agc                                             23

<210> SEQ ID NO 34
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 34
taccagcatc tgcaggaagg                                                 20

<210> SEQ ID NO 35
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 35
```

```
gacttctcat ccccgaagtc c                                               21
```

<210> SEQ ID NO 36
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 36

```
gacgccatca tcgtcatagg                                                 20
```

<210> SEQ ID NO 37
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 37

```
atgttctcct ccaggatctt cc                                              22
```

<210> SEQ ID NO 38
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 38

```
aagaactccg agtagggagt cg                                              22
```

<210> SEQ ID NO 39
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 39

```
tgcgttgtac ttctccttga gc                                              22
```

<210> SEQ ID NO 40
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 40

```
cctgactatc ctccctctga cc                                              22
```

<210> SEQ ID NO 41
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 41

```
gctgctgtac ttgaggttgt cc                                              22
```

<210> SEQ ID NO 42
<211> LENGTH: 22
<212> TYPE: DNA
<213> ORGANISM: Artificial Sequence
<220> FEATURE:

<223> OTHER INFORMATION: synthetically generated oligonucleotide

<400> SEQUENCE: 42
gtacagcacc aagttcctca gc                                    22

<210> SEQ ID NO 43
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 43
actggagtct cgagaacaca cc                                    22

<210> SEQ ID NO 44
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 44
gaacaaagtc ccctacgaga gc                                    22

<210> SEQ ID NO 45
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 45
ggttgttgtg gagtctcatt cg                                    22

<210> SEQ ID NO 46
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 46
gtggtaacgg aaaacctgaa gc                                    22

<210> SEQ ID NO 47
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 47
ctcatcacac agcacataac agc                                   23

<210> SEQ ID NO 48
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 48
gccatgaatc tacacaacaa cg                                    22

<210> SEQ ID NO 49

<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 49
ctgactacat gggtgttgta gcc                                            23

<210> SEQ ID NO 50
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 50
actccactca cggcaaattc                                                20

<210> SEQ ID NO 51
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 51
cacattgggg gtaggaacac                                                20

<210> SEQ ID NO 52
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 52
aagaccctgc ttgaggacaa                                                20

<210> SEQ ID NO 53
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 53
gagtgggata gccacatcgt                                                20

<210> SEQ ID NO 54
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 54
gagctcatcg gtgacatgaa                                                20

<210> SEQ ID NO 55
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 55

-continued gctcgaggac tgtcaaggtc                                              20

<210> SEQ ID NO 56
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 56
ggagatcctc ccaggaaaag                                              20

<210> SEQ ID NO 57
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 57
ggagcagcag ctagaggaga                                              20

<210> SEQ ID NO 58
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 58
cagaagatcg gacaggaagc                                              20

<210> SEQ ID NO 59
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 59
cagaaatcct cctgactctg                                              20

<210> SEQ ID NO 60
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 60
gcggttgatg gagttgctat                                              20

<210> SEQ ID NO 61
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 61
aaggcaaatc ttggcacatc                                              20

<210> SEQ ID NO 62
<211> LENGTH: 21
<212> TYPE: DNA
<213> ORGANISM: Artificial Sequence
<220> FEATURE:

```
<223> OTHER INFORMATION: synthetically generated oligonucleotide

<400> SEQUENCE: 62
gctacaacgt gaccaagatg c                                              21

<210> SEQ ID NO 63
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 63
caaacccaaa ttctctcagg ac                                             22

<210> SEQ ID NO 64
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 64
cctggtggag agtggtgatt                                                20

<210> SEQ ID NO 65
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 65
cagtaatggc cccacactct                                                20

<210> SEQ ID NO 66
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 66
aagtccatgg gaactagcac ag                                             22

<210> SEQ ID NO 67
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 67
tctttcctag ctctggaagc tg                                             22

<210> SEQ ID NO 68
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 68
tgtggtcagt gctgtgctg                                                 19

<210> SEQ ID NO 69
```

-continued

<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 69
cactgagtag gtcaccatcc ac                                         22

<210> SEQ ID NO 70
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 70
atatggagcg ctttaagtac cc                                         22

<210> SEQ ID NO 71
<211> LENGTH: 18
<212> TYPE: DNA
<213> ORGANISM: Artificial Sequence
<220> FEATURE:
<223> OTHER INFORMATION: synthetically generated oligonucleotide

<400> SEQUENCE: 71
caccgcgatg gacttgac                                              18

<210> SEQ ID NO 72
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 72
accccagtac tcctctctga gc                                         22

<210> SEQ ID NO 73
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 73
cattcctcca aattcaatgt cc                                         22

<210> SEQ ID NO 74
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 74
gcatgctttt cagttttcaa cc                                         22

<210> SEQ ID NO 75
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 75

-continued

```
cctttaggta atttcccatc tgc                                             23

<210> SEQ ID NO 76
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 76
ggccataatc ttgtgttagc                                                 20

<210> SEQ ID NO 77
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 77
ataggaaaag cacaaatgga                                                 20

<210> SEQ ID NO 78
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 78
tggatggatg gatgatagat                                                 20

<210> SEQ ID NO 79
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 79
tcctgcagtg tgtactcaga                                                 20

<210> SEQ ID NO 80
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 80
tgttcgggac atcattacca                                                 20

<210> SEQ ID NO 81
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 81
gcccacgtac ctccttcata                                                 20

<210> SEQ ID NO 82
<211> LENGTH: 20
<212> TYPE: DNA
<213> ORGANISM: Artificial Sequence
<220> FEATURE:
```

```
<223> OTHER INFORMATION: synthetically generated oligonucleotide

<400> SEQUENCE: 82
cgacatcatg gaaacccttt                                              20

<210> SEQ ID NO 83
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 83
ggagcggaag tggtctacag                                              20

<210> SEQ ID NO 84
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 84
ttacttccgg tcccctttct                                              20

<210> SEQ ID NO 85
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 85
ttcctggtgt tgggctactc                                              20

<210> SEQ ID NO 86
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 86
tccctctcat caccaattcc                                              20

<210> SEQ ID NO 87
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 87
gcagcaccac cttatcctgt                                              20

<210> SEQ ID NO 88
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 88
cacttggcct caccttcact                                              20

<210> SEQ ID NO 89
```

```
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 89
gccttggatc ttgctctttg                                             20

<210> SEQ ID NO 90
<211> LENGTH: 88
<212> TYPE: PRT
<213> ORGANISM: Artificial Sequence
<220> FEATURE:
<223> OTHER INFORMATION: fragment of human DKK2 protein

<400> SEQUENCE: 90

Met Ser His Ile Lys Gly His Glu Gly Asp Pro Cys Leu Arg Ser Ser
 1               5                  10                  15

Asp Cys Ile Glu Gly Phe Cys Cys Ala Arg His Phe Trp Thr Lys Ile
            20                  25                  30

Cys Lys Pro Val Leu His Gln Gly Glu Val Cys Thr Lys Gln Arg Lys
        35                  40                  45

Lys Gly Ser His Gly Leu Glu Ile Phe Gln Arg Cys Asp Cys Ala Lys
    50                  55                  60

Gly Leu Ser Cys Lys Val Trp Lys Asp Ala Thr Tyr Ser Ser Lys Ala
65                  70                  75                  80

Arg Leu His Val Cys Gln Lys Ile
                85

<210> SEQ ID NO 91
<211> LENGTH: 88
<212> TYPE: PRT
<213> ORGANISM: Artificial Sequence
<220> FEATURE:
<223> OTHER INFORMATION: fragment of mouse DKK2 protein

<400> SEQUENCE: 91

Met Pro His Ile Lys Gly His Glu Gly Asp Pro Cys Leu Arg Ser Ser
 1               5                  10                  15

Asp Cys Ile Asp Gly Phe Cys Cys Ala Arg His Phe Trp Thr Lys Ile
            20                  25                  30

Cys Lys Pro Val Leu His Gln Gly Glu Val Cys Thr Lys Gln Arg Lys
        35                  40                  45

Lys Gly Ser His Gly Leu Glu Ile Phe Gln Arg Cys Asp Cys Ala Lys
    50                  55                  60

Gly Leu Ser Cys Lys Val Trp Lys Asp Ala Thr Tyr Ser Ser Lys Ala
65                  70                  75                  80

Arg Leu His Val Cys Gln Lys Ile
                85

<210> SEQ ID NO 92
<211> LENGTH: 259
<212> TYPE: PRT
<213> ORGANISM: Homo sapiens DKK2

<400> SEQUENCE: 92

Met Ala Ala Leu Met Arg Ser Lys Asp Ser Cys Cys Leu Leu Leu
 1               5                  10                  15

Leu Ala Ala Val Leu Met Val Glu Ser Ser Gln Ile Gly Ser Ser Arg
            20                  25                  30
```

Ala Lys Leu Asn Ser Ile Lys Ser Ser Leu Gly Gly Glu Thr Pro Gly
         35                  40                  45

Gln Ala Ala Asn Arg Ser Ala Gly Met Tyr Gln Gly Leu Ala Phe Gly
     50                  55                  60

Gly Ser Lys Lys Gly Lys Asn Leu Gly Gln Ala Tyr Pro Cys Ser Ser
 65                  70                  75                  80

Asp Lys Glu Cys Glu Val Gly Arg Tyr Cys His Ser Pro His Gln Gly
                 85                  90                  95

Ser Ser Ala Cys Met Val Cys Arg Arg Lys Lys Lys Arg Cys His Arg
            100                 105                 110

Asp Gly Met Cys Cys Pro Ser Thr Arg Cys Asn Asn Gly Ile Cys Ile
        115                 120                 125

Pro Val Thr Glu Ser Ile Leu Thr Pro His Ile Pro Ala Leu Asp Gly
    130                 135                 140

Thr Arg His Arg Asp Arg Asn His Gly His Tyr Ser Asn His Asp Leu
145                 150                 155                 160

Gly Trp Gln Asn Leu Gly Arg Pro His Thr Lys Met Ser His Ile Lys
                165                 170                 175

Gly His Glu Gly Asp Pro Cys Leu Arg Ser Ser Asp Cys Ile Glu Gly
            180                 185                 190

Phe Cys Cys Ala Arg His Phe Trp Thr Lys Ile Cys Lys Pro Val Leu
        195                 200                 205

His Gln Gly Glu Val Cys Thr Lys Gln Arg Lys Lys Gly Ser His Gly
    210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                245                 250                 255

Gln Lys Ile

<210> SEQ ID NO 93
<211> LENGTH: 259
<212> TYPE: PRT
<213> ORGANISM: Mus musculus DKK2

<400> SEQUENCE: 93

Met Ala Ala Leu Met Arg Val Lys Asp Ser Ser Arg Cys Leu Leu Leu
 1               5                  10                  15

Leu Ala Ala Val Leu Met Val Glu Ser Ser Gln Leu Gly Ser Ser Arg
                 20                  25                  30

Ala Lys Leu Asn Ser Ile Lys Ser Ser Leu Gly Gly Glu Thr Pro Ala
         35                  40                  45

Gln Ser Ala Asn Arg Ser Ala Gly Met Asn Gln Gly Leu Ala Phe Gly
     50                  55                  60

Gly Ser Lys Lys Gly Lys Ser Leu Gly Gln Ala Tyr Pro Cys Ser Ser
 65                  70                  75                  80

Asp Lys Glu Cys Glu Val Gly Arg Tyr Cys His Ser Pro His Gln Gly
                 85                  90                  95

Ser Ser Ala Cys Met Leu Cys Arg Arg Lys Lys Lys Arg Cys His Arg
            100                 105                 110

Asp Gly Met Cys Cys Pro Gly Thr Arg Cys Asn Asn Gly Ile Cys Ile
        115                 120                 125

Pro Val Thr Glu Ser Ile Leu Thr Pro His Ile Pro Ala Leu Asp Gly
    130                 135                 140

Thr Arg His Arg Asp Arg Asn His Gly His Tyr Ser Asn His Asp Leu

-continued

```
145                 150                 155                 160

Gly Trp Gln Asn Leu Gly Arg Pro His Ser Lys Met Pro His Ile Lys
                165                 170                 175

Gly His Glu Gly Asp Pro Cys Leu Arg Ser Ser Asp Cys Ile Asp Gly
                180                 185                 190

Phe Cys Cys Ala Arg His Phe Trp Thr Lys Ile Cys Lys Pro Val Leu
        195                 200                 205

His Gln Gly Glu Val Cys Thr Lys Gln Arg Lys Lys Gly Ser His Gly
    210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                245                 250                 255

Gln Lys Ile
```